United States Patent [19]

Kawasaki et al.

[11] Patent Number: 5,547,864
[45] Date of Patent: Aug. 20, 1996

[54] CORYNEFORM BACTERIA DEFICIENT IN A CELL SURFACE PROTEIN

[75] Inventors: Hisashi Kawasaki; Makoto Tsuchiya; Kiyoshi Miwa; Yoshio Kawahara, all of Kawasaki, Japan

[73] Assignee: Ajinomoto Co., Inc., Tokyo, Japan

[21] Appl. No.: 295,670

[22] PCT Filed: Jan. 13, 1994

[86] PCT No.: PCT/JP94/00039

§ 371 Date: Sep. 8, 1994

§ 102(e) Date: Sep. 8, 1994

[87] PCT Pub. No.: WO94/15963

PCT Pub. Date: Jul. 21, 1994

[30] Foreign Application Priority Data

Jan. 13, 1993 [JP] Japan .................. 5-004069

[51] Int. Cl.⁶ .................. C12P 1/4; C12P 13/4; C12N 1/20; C07K 14/34
[52] U.S. Cl. .................. 435/170; 435/106; 435/252.32; 530/350
[58] Field of Search .................. 435/170, 252.32, 435/106

[56] References Cited

FOREIGN PATENT DOCUMENTS

| | | |
|---|---|---|
| 2667875 | 4/1992 | France . |
| 57-22558 | 2/1982 | Japan . |
| 57-134500 | 8/1982 | Japan . |
| 57-183799 | 11/1982 | Japan . |
| 58-35197 | 3/1983 | Japan . |
| 58-67699 | 4/1983 | Japan . |
| 58-77895 | 5/1983 | Japan . |
| 58-192900 | 11/1983 | Japan . |
| 62-151184 | 7/1987 | Japan . |
| 62-244382 | 10/1987 | Japan . |
| 2109985 | 4/1990 | Japan . |
| 2207791 | 8/1990 | Japan . |
| 4271780 | 9/1992 | Japan . |
| WO93/03158 | 2/1993 | WIPO . |

OTHER PUBLICATIONS

Peyret, J. L. (1993) "Characterization of the cspB gene encoding PS2, an ordered surface–layer protein in *Corynebacterium glutamicum*" *Mol. Microbiol.* 9(1):97–109.

*Primary Examiner*—Robert A. Wax
*Assistant Examiner*—Kawai Lau
*Attorney, Agent, or Firm*—Oblon, Spivak, McClelland, Maier, & Neustadt, P.C.

[57] ABSTRACT

A DNA fragment containing a gene coding for a novel cell surface layer protein derived from *Brevibacterium lactofermentum* and having two sequences of:

(1) Thr-Leu-Arg-Gln-His-Tyr-Ser-Ser-Leu-Ile-Pro-Asn-Leu-Phe-Ile-Ala-Ala-Val-Gly-Asn-Ile-Asn-Glu-Leu-Asn-Asn-Ala-Asp-Gln-    Ala-Ala-Arg-Glu-Leu-Phe-Leu-Asp-Trp-Asp-Thr (SEQ ID NO: 1) and:

(2) Asn-Lys-Thr-Asp-Phe-Ala-Glu-Ile-Glu-Leu-Tyr-Asp-Val-Leu-Tyr-Thr-Asp-Ala-Asp-Ile-Ser-Gly-Asp-Ala-Pro-Leu-Leu-Ala-Pro-Ala-Tyr-Lys (SEQ ID NO: 2)

in the molecule, and having a molecular weight of about 63,000 dalton is introduced into Coryneform bacteria to obtain a transformant, or originate a mutant strain being sufficient in the novel cell surface layer protein, which is used for producing a useful substance such as an L-amino acid by an L-amino acid fermentation method.

8 Claims, 4 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 40 amino acids
( B ) TYPE: amino acid
( C ) STRANDEDNESS: Not Relevant
( D ) TOPOLOGY: linear ( i i ) MOLECULE TYPE: protein ( v i ) ORIGINAL SOURCE:
( A ) ORGANISM: Brevibacterium lactofermentum
( B ) STRAIN: 2256 (ATCC 13869)

( x i ) SEQUENCE DESCRIPTION: SEQ ID NO:1:

```
Thr Leu Arg Gln His Tyr Ser Ser Leu Ile Pro Asn Leu Phe Ile Ala
 1               5                  10                  15

Ala Val Gly Asn Ile Asn Glu Leu Asn Asn Ala Asp Gln Ala Ala Arg
            20                  25                  30

Glu Leu Phe Leu Asp Trp Asp Thr
            35                  40
```

( 2 ) INFORMATION FOR SEQ ID NO:2:

( i ) SEQUENCE CHARACTERISTICS:
( A ) LENGTH: 32 amino acids
( B ) TYPE: amino acid
( C ) STRANDEDNESS: Not Relevant
( D ) TOPOLOGY: linear ( i i ) MOLECULE TYPE: protein ( v i ) ORIGINAL SOURCE:
( A ) ORGANISM: Brevibacterium lactofermentum
( B ) STRAIN: 2256 (ATCC 13869)

( x i ) SEQUENCE DESCRIPTION: SEQ ID NO:2:

```
Asn Lys Thr Asp Phe Ala Glu Ile Glu Leu Tyr Asp Val Leu Tyr Thr
 1               5                  10                  15

Asp Ala Asp Ile Ser Gly Asp Ala Pro Leu Leu Ala Pro Ala Tyr Lys
            20                  25                  30
```

( 2 ) INFORMATION FOR SEQ ID NO:3:

( i ) SEQUENCE CHARACTERISTICS:
( A ) LENGTH: 30 base pairs
( B ) TYPE: nucleic acid
( C ) STRANDEDNESS: double
( D ) TOPOLOGY: linear ( i i ) MOLECULE TYPE: other nucleic acid ( x i ) SEQUENCE DESCRIPTION: SEQ ID NO:3:

TTCATCGCTG CTGTCGGCAA CATCAACGAG                30

( 2 ) INFORMATION FOR SEQ ID NO:4:

( i ) SEQUENCE CHARACTERISTICS:
( A ) LENGTH: 48 base pairs ( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Brevibacterium lactofermentum
( B ) STRAIN: 2256 (ATCC 13869)

( x i ) SEQUENCE DESCRIPTION: SEQ ID NO:4:

| | | | | |
|---|---|---|---|---|
| AACAATGCAG | ATCAGGCTGC | ACGTGAGCTC | TTCCTCGATT | GGGACACC | 48 |

( 2 ) INFORMATION FOR SEQ ID NO:5:

( i ) SEQUENCE CHARACTERISTICS:
( A ) LENGTH: 2653 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Brevibacterium lactofermentum
( B ) STRAIN: 2256 (ATCC 13869)

( i x ) FEATURE:
( A ) NAME/KEY: CDS
( B ) LOCATION: 912..2402

( x i ) SEQUENCE DESCRIPTION: SEQ ID NO:5:

| | | | | | |
|---|---|---|---|---|---|
| ACTGGGAGGC | TATCTCCATT | GGGCGGTGCT | GTCATCGTTG | GCAGCTTTTC | CATCCTGGAT | 60 |
| GGGGTTCTGG | GCAGGACTGC | CTTTGGCGGT | CCTGTTAAAC | GTCGCGGTTT | GGTTGTACAC | 120 |
| CATCTATTCG | ATGGCAACCA | TGGATGAAGA | TGATGCGCGG | CTGCAAGGGG | AAACAGCTCC | 180 |
| GTCATACTTT | GAACGGATGC | TGTGGGTGTG | CAAAATTTCG | TTGTGGGGCA | TTGATTTTTG | 240 |
| GAAAAGTAT | CGCATCGCAT | TAGCGATGTC | TAAATCTTGG | CTGAAACCAT | TACATTTGCT | 300 |
| GTGTGCGAAC | TGTATATCAG | CTGATATTGC | GCCTAAATTC | CTGTGAATTA | GCTGATTTAG | 360 |
| TACTTTTCGG | AGGTGTCTAT | TCTTACCAAA | TTCGTCAAGT | TGTGGGTAGA | GTCACCTGAA | 420 |
| TATTAATTGC | ACCGCACCGG | GTGATATATG | CTTATTTGCC | TCAAGTAGTT | CGAGGTTAAG | 480 |
| TGTATTTTAG | GTGAACCAAA | TTTCAGCTTC | GGGTAGAAGA | CTTTCGATGC | GCTTCAGAGC | 540 |
| TTCTATTGGG | AAATCTGACA | CCACTTGATT | AAATAGCCTA | CCCCCGAATT | GGGGAGATTG | 600 |
| GTCATTTTTT | GCTGTGAAGG | TAGTTTTGAT | GCATATGACC | TGCCGTTTAT | AAAGAAATGT | 660 |
| AACGTGATCA | GATCGATATA | AAGAACAGTT | GTACTCAGGT | TTGAAGGCAT | CTCCGATTC | 720 |
| GCTGGCAAAT | CTCATTGTCG | GCTTACAGTT | TTCTCAACGA | CAGGCGTGCT | AAGCTGCTAG | 780 |
| TTCAGGTGGC | CTAGTGAGTG | GCGTTTACTT | GGATAAAAGT | AATCCCATGT | CGTGATCAGC | 840 |
| CATTTTGGGT | TGTTTCCATA | GCAATCCAAA | GGTTTCGTCT | TTCGATACCT | ATTCAAGGAG | 900 |
| CCTTCGCCTC | T ATG TTT AAC AAC CGT ATC CGC ACT GCA GCT CTT GCT GGT | | | | | 950 |
| | Met Phe Asn Asn Arg Ile Arg Thr Ala Ala Leu Ala Gly | | | | | |
| | 1 5 10 | | | | | |

| GCA | ATC | GCA | ATC | TCC | ACC | GCA | GCT | TCC | GGC | GTA | GCT | ATC | CCA | GCA | TTC | 998 |
|---|---|---|---|---|---|---|---|---|---|---|---|---|---|---|---|---|
| Ala | Ile | Ala | Ile | Ser | Thr | Ala | Ala | Ser | Gly | Val | Ala | Ile | Pro | Ala | Phe | |
| | 15 | | | | 20 | | | | | 25 | | | | | | |

| GCT | CAG | GAG | ACC | AAC | CCA | ACC | TTC | AAC | ATC | ACC | AAC | GGC | TTC | AAC | GAT | 1046 |
|---|---|---|---|---|---|---|---|---|---|---|---|---|---|---|---|---|
| Ala | Gln | Glu | Thr | Asn | Pro | Thr | Phe | Asn | Ile | Thr | Asn | Gly | Phe | Asn | Asp | |
| 30 | | | | | 35 | | | | 40 | | | | | | 45 | |

| GCT | GAT | GGA | TCC | ACC | ATC | CAG | CCA | GTT | GAG | CCA | GTT | AAC | CAC | ACC | GAG | 1094 |
|---|---|---|---|---|---|---|---|---|---|---|---|---|---|---|---|---|
| Ala | Asp | Gly | Ser | Thr | Ile | Gln | Pro | Val | Glu | Pro | Val | Asn | His | Thr | Glu | |
| | | | 50 | | | | 55 | | | | | 60 | | | | |

| | | | | | | | | | | | | | | | | |
|---|---|---|---|---|---|---|---|---|---|---|---|---|---|---|---|---|
| GAA | ACC | CTC | CGC | GAC | CTG | ACT | GAC | TCC | ACC | GGC | GCT | TAC | CTG | GAA | GAG | 1142 |
| Glu | Thr | Leu | Arg 65 | Asp | Leu | Thr | Asp | Ser 70 | Thr | Gly | Ala | Tyr | Leu 75 | Glu | Glu | |
| TTC | CAG | TAC | GGC | AAC | GTT | GAG | GAA | ATC | GTT | GAA | GCA | TAC | CTG | CAG | GTT | 1190 |
| Phe | Gln | Tyr 80 | Gly | Asn | Val | Glu | Glu | Ile 85 | Val | Glu | Ala | Tyr | Leu 90 | Gln | Val | |
| CAG | GCT | TCC | GCA | GAC | GGA | TTC | GAT | CCT | TCT | GAG | CAG | GCT | GCT | TAC | GAG | 1238 |
| Gln | Ala | Ser 95 | Ala | Asp | Gly | Phe | Asp | Pro 100 | Ser | Glu | Gln | Ala | Ala 105 | Tyr | Glu | |
| GCT | TTC | GAG | GCT | GCT | CGC | GTT | CGT | GCA | TCC | CAG | GAG | CTC | GCG | GCT | TCC | 1286 |
| Ala | Phe 110 | Glu | Ala | Ala | Arg 115 | Val | Arg | Ala | Ser | Gln 120 | Glu | Leu | Ala | Ala | Ser 125 | |
| GCT | GAG | ACC | ATC | ACT | AAG | ACC | CGC | GAG | TCC | GTT | GCT | TAC | GCA | CTC | AAG | 1334 |
| Ala | Glu | Thr | Ile | Thr 130 | Lys | Thr | Arg | Glu | Ser 135 | Val | Ala | Tyr | Ala | Leu 140 | Lys | |
| GCT | GAC | CGC | GAA | GCT | ACC | GCA | GCT | TTC | GAG | GCT | TAC | CTC | AGC | GCT | CTT | 1382 |
| Ala | Asp | Arg | Glu 145 | Ala | Thr | Ala | Ala | Phe 150 | Glu | Ala | Tyr | Leu | Ser 155 | Ala | Leu | |
| CGT | CAG | GTT | TCA | GTC | ATC | AAC | GAT | CTG | ATC | GCT | GAT | GCT | AAC | GCC | AAG | 1430 |
| Arg | Gln | Val 160 | Ser | Val | Ile | Asn | Asp 165 | Leu | Ile | Ala | Asp | Ala 170 | Asn | Ala | Lys | |
| AAC | AAG | ACT | GAC | TTT | GCA | GAG | ATC | GAG | CTC | TAC | GAT | GTC | CTT | TAC | ACC | 1478 |
| Asn | Lys 175 | Thr | Asp | Phe | Ala | Glu 180 | Ile | Glu | Leu | Tyr | Asp 185 | Val | Leu | Tyr | Thr | |
| GAC | GCG | GAC | ATC | TCT | GGC | GAT | GCT | CCA | CTT | CTT | GCT | CCT | GCA | TAC | AAG | 1526 |
| Asp 190 | Ala | Asp | Ile | Ser | Gly 195 | Asp | Ala | Pro | Leu | Leu 200 | Ala | Pro | Ala | Tyr | Lys 205 | |
| GAG | CTG | AAG | GAC | CTT | CAG | GCT | GAG | GTT | GAC | GCA | GAC | TTC | GAG | TGG | TTG | 1574 |
| Glu | Leu | Lys | Asp | Leu 210 | Gln | Ala | Glu | Val | Asp 215 | Ala | Asp | Phe | Glu | Trp 220 | Leu | |
| GGC | GAG | TTC | GCA | ATT | GAT | AAC | AAT | GAA | GAC | AAC | TAC | GTC | ATT | CGT | ACT | 1622 |
| Gly | Glu | Phe | Ala 225 | Ile | Asp | Asn | Asn | Glu 230 | Asp | Asn | Tyr | Val | Ile 235 | Arg | Thr | |
| CAC | ATC | CCT | GCT | GTA | GAG | GCA | CTC | AAG | GCA | GCG | ATC | GAT | TCA | CTG | GTC | 1670 |
| His | Ile | Pro 240 | Ala | Val | Glu | Ala | Leu 245 | Lys | Ala | Ala | Ile | Asp 250 | Ser | Leu | Val | |
| GAC | ACC | GTT | GAG | CCA | CTT | CGT | GCA | GAC | GCT | ATC | GCT | AAG | AAC | ATC | GAG | 1718 |
| Asp | Thr 255 | Val | Glu | Pro | Leu | Arg 260 | Ala | Asp | Ala | Ile | Ala 265 | Lys | Asn | Ile | Glu | |
| GCT | CAG | AAG | TCT | GAC | GTT | CTG | GTT | CCC | CAG | CTC | TTC | CTC | GAG | CGT | GCA | 1766 |
| Ala 270 | Gln | Lys | Ser | Asp | Val 275 | Leu | Val | Pro | Gln | Leu 280 | Phe | Leu | Glu | Arg | Ala 285 | |
| ACT | GCA | CAG | CGC | GAC | ACC | CTG | CGT | GTT | GTA | GAG | GCA | ATC | TTC | TCT | ACC | 1814 |
| Thr | Ala | Gln | Arg | Asp 290 | Thr | Leu | Arg | Val | Val 295 | Glu | Ala | Ile | Phe | Ser 300 | Thr | |
| TCT | GCT | CGT | TAC | GTT | GAA | CTC | TAC | GAG | AAC | GTC | GAG | AAC | GTT | AAC | GTT | 1862 |
| Ser | Ala | Arg | Tyr 305 | Val | Glu | Leu | Tyr | Glu 310 | Asn | Val | Glu | Asn | Val 315 | Asn | Val | |
| GAG | AAC | AAG | ACC | CTT | CGC | CAG | CAC | TAC | TCT | TCC | CTG | ATC | CCT | AAC | CTC | 1910 |
| Glu | Asn | Lys 320 | Thr | Leu | Arg | Gln | His 325 | Tyr | Ser | Ser | Leu | Ile 330 | Pro | Asn | Leu | |
| TTC | ATC | GCA | GCG | GTT | GGC | AAC | ATC | AAC | GAG | CTC | AAC | AAT | GCA | GAT | CAG | 1958 |
| Phe | Ile 335 | Ala | Ala | Val | Gly | Asn 340 | Ile | Asn | Glu | Leu | Asn 345 | Asn | Ala | Asp | Gln | |
| GCT | GCA | CGT | GAG | CTC | TTC | CTC | GAT | TGG | GAC | ACC | GAC | CTC | ACC | ACC | AAC | 2006 |
| Ala 350 | Ala | Arg | Glu | Leu | Phe 355 | Leu | Asp | Trp | Asp | Thr 360 | Asp | Leu | Thr | Thr | Asn 365 | |
| GAT | GAG | GAC | GAA | GCT | TAC | TAC | CAG | GCT | AAG | CTC | GAC | TTC | GCT | ATC | GAG | 2054 |
| Asp | Glu | Asp | Glu | Ala 370 | Tyr | Tyr | Gln | Ala | Lys 375 | Leu | Asp | Phe | Ala | Ile 380 | Glu | |

| | | | | | | | | | | | | | | | | |
|---|---|---|---|---|---|---|---|---|---|---|---|---|---|---|---|---|
| ACC | TAC | GCA | AAG | ATC | CTG | ATC | AAC | GGT | GAA | GTT | TGG | CAG | GAG | CCA | CTC | 2102 |
| Thr | Tyr | Ala | Lys | Ile | Leu | Ile | Asn | Gly | Glu | Val | Trp | Gln | Glu | Pro | Leu | |
| | | | 385 | | | | | 390 | | | | | 395 | | | |
| GCT | TAC | GTC | CAG | AAC | CTG | GAT | GCA | GGC | GCA | CGT | CAG | GAA | GCA | GCT | GAC | 2150 |
| Ala | Tyr | Val | Gln | Asn | Leu | Asp | Ala | Gly | Ala | Arg | Gln | Glu | Ala | Ala | Asp | |
| | | 400 | | | | | 405 | | | | | 410 | | | | |
| CGC | GAA | GCA | GAG | CGC | GCT | GAC | GCA | GCA | TAT | TGC | CGC | GCT | GAG | CAG | CTC | 2198 |
| Arg | Glu | Ala | Glu | Arg | Ala | Asp | Ala | Ala | Tyr | Cys | Arg | Ala | Glu | Gln | Leu | |
| | 415 | | | | | 420 | | | | | 425 | | | | | |
| CGC | ATC | GCT | CAG | GAA | GCA | GCT | GAC | GCT | CAG | AAG | GCT | TTC | GCT | GAG | GCT | 2246 |
| Arg | Ile | Ala | Gln | Glu | Ala | Ala | Asp | Ala | Gln | Lys | Ala | Phe | Ala | Glu | Ala | |
| 430 | | | | | 435 | | | | | 440 | | | | | 445 | |
| CTG | CTA | ATG | CCA | GGC | AAC | AAC | GAC | AAC | GGT | GGC | GAC | AAC | TCC | TCC | GAC | 2294 |
| Leu | Leu | Met | Pro | Gly | Asn | Asn | Asp | Asn | Gly | Gly | Asp | Asn | Ser | Ser | Asp | |
| | | | | 450 | | | | | 455 | | | | | 460 | | |
| GAC | AAG | GGA | ACC | GGT | TCT | TCC | GAC | ATC | GGA | ACC | TGG | GGA | CCT | TTC | GCA | 2342 |
| Asp | Lys | Gly | Thr | Gly | Ser | Ser | Asp | Ile | Gly | Thr | Trp | Gly | Pro | Phe | Ala | |
| | | | 465 | | | | | 470 | | | | | 475 | | | |
| GCA | ATT | GCA | GCT | ATC | ATC | GCA | GCA | ATC | GCA | GCT | ATC | TTT | CCA | TTC | CTC | 2390 |
| Ala | Ile | Ala | Ala | Ile | Ile | Ala | Ala | Ile | Ala | Ala | Ile | Phe | Pro | Phe | Leu | |
| | | 480 | | | | | 485 | | | | | 490 | | | | |
| TCC | GGT | ATC | GGT | TAAGTTCTAA | TTTCGAACCG | AGATAGCTAA | AAGTTAAACC | | | | | | | | | 2442 |
| Ser | Gly | Ile | Gly | | | | | | | | | | | | | |
| | | 495 | | | | | | | | | | | | | | |

ACCTCCTTTC CTTGGCCGGG AGGTGGTTTT TCCCTTGTTT AATTGCACTA AAGAAAAGC  2502

CACCTCCTGC TTTAAGGAG GTGGCTTTTC TTCGTCTACC TAGTTGAAAT AGAGGTGGGC  2562

GTCGATAAGC AAAAATCTTT TGCTTTTAAG GGAACGTGAT AATCGGCTTA ATGACCTCCC  2622

GCTGGCAGAA TCTGCAAAGG CATCATTGAT C  2653

( 2 ) INFORMATION FOR SEQ ID NO:6:

( i ) SEQUENCE CHARACTERISTICS:
        ( A ) LENGTH: 497 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met | Phe | Asn | Asn | Arg | Ile | Arg | Thr | Ala | Ala | Leu | Ala | Gly | Ala | Ile | Ala |
| 1 | | | | 5 | | | | | 10 | | | | | 15 | |
| Ile | Ser | Thr | Ala | Ala | Ser | Gly | Val | Ala | Ile | Pro | Ala | Phe | Ala | Gln | Glu |
| | | | | 20 | | | | 25 | | | | | 30 | | |
| Thr | Asn | Pro | Thr | Phe | Asn | Ile | Thr | Asn | Gly | Phe | Asn | Asp | Ala | Asp | Gly |
| | | | 35 | | | | | 40 | | | | | 45 | | |
| Ser | Thr | Ile | Gln | Pro | Val | Glu | Pro | Val | Asn | His | Thr | Glu | Glu | Thr | Leu |
| | | 50 | | | | | 55 | | | | | 60 | | | |
| Arg | Asp | Leu | Thr | Asp | Ser | Thr | Gly | Ala | Tyr | Leu | Glu | Glu | Phe | Gln | Tyr |
| 65 | | | | | 70 | | | | | 75 | | | | | 80 |
| Gly | Asn | Val | Glu | Glu | Ile | Val | Glu | Ala | Tyr | Leu | Gln | Val | Gln | Ala | Ser |
| | | | | 85 | | | | | 90 | | | | | 95 | |
| Ala | Asp | Gly | Phe | Asp | Pro | Ser | Glu | Gln | Ala | Ala | Tyr | Glu | Ala | Phe | Glu |
| | | | 100 | | | | | 105 | | | | | 110 | | |
| Ala | Ala | Arg | Val | Arg | Ala | Ser | Gln | Glu | Leu | Ala | Ala | Ser | Ala | Glu | Thr |
| | | 115 | | | | | 120 | | | | | 125 | | | |
| Ile | Thr | Lys | Thr | Arg | Glu | Ser | Val | Ala | Tyr | Ala | Leu | Lys | Ala | Asp | Arg |
| | 130 | | | | | 135 | | | | | 140 | | | | |

| | | | | | | | | | | | | | | | |
|---|---|---|---|---|---|---|---|---|---|---|---|---|---|---|---|
| Glu 145 | Ala | Thr | Ala | Ala | Phe 150 | Glu | Ala | Tyr | Leu | Ser 155 | Ala | Leu | Arg | Gln | Val 160 |
| Ser | Val | Ile | Asn | Asp 165 | Leu | Ile | Ala | Asp | Ala 170 | Asn | Ala | Lys | Asn | Lys 175 | Thr |
| Asp | Phe | Ala | Glu 180 | Ile | Glu | Leu | Tyr | Asp 185 | Val | Leu | Tyr | Thr | Asp 190 | Ala | Asp |
| Ile | Ser | Gly 195 | Asp | Ala | Pro | Leu 200 | Leu | Ala | Pro | Ala | Tyr 205 | Lys | Glu | Leu | Lys |
| Asp | Leu 210 | Gln | Ala | Glu | Val | Asp 215 | Ala | Asp | Phe | Glu | Trp 220 | Leu | Gly | Glu | Phe |
| Ala 225 | Ile | Asp | Asn | Asn | Glu 230 | Asp | Asn | Tyr | Val | Ile 235 | Arg | Thr | His | Ile | Pro 240 |
| Ala | Val | Glu | Ala | Leu 245 | Lys | Ala | Ala | Ile | Asp 250 | Ser | Leu | Val | Asp | Thr 255 | Val |
| Glu | Pro | Leu | Arg 260 | Ala | Asp | Ala | Ile | Ala 265 | Lys | Asn | Ile | Glu | Ala 270 | Gln | Lys |
| Ser | Asp | Val 275 | Leu | Val | Pro | Gln | Leu 280 | Phe | Leu | Glu | Arg | Ala 285 | Thr | Ala | Gln |
| Arg | Asp 290 | Thr | Leu | Arg | Val | Val 295 | Glu | Ala | Ile | Phe | Ser 300 | Thr | Ser | Ala | Arg |
| Tyr 305 | Val | Glu | Leu | Tyr | Glu 310 | Asn | Val | Glu | Asn | Val 315 | Asn | Val | Glu | Asn | Lys 320 |
| Thr | Leu | Arg | Gln | His 325 | Tyr | Ser | Ser | Leu | Ile 330 | Pro | Asn | Leu | Phe | Ile 335 | Ala |
| Ala | Val | Gly | Asn 340 | Ile | Asn | Glu | Leu | Asn 345 | Asn | Ala | Asp | Gln | Ala 350 | Ala | Arg |
| Glu | Leu | Phe 355 | Leu | Asp | Trp | Asp | Thr 360 | Asp | Leu | Thr | Thr | Asn 365 | Asp | Glu | Asp |
| Glu | Ala 370 | Tyr | Tyr | Gln | Ala | Lys 375 | Leu | Asp | Phe | Ala | Ile 380 | Glu | Thr | Tyr | Ala |
| Lys 385 | Ile | Leu | Ile | Asn | Gly 390 | Glu | Val | Trp | Gln | Glu 395 | Pro | Leu | Ala | Tyr | Val 400 |
| Gln | Asn | Leu | Asp | Ala 405 | Gly | Ala | Arg | Gln | Glu 410 | Ala | Ala | Asp | Arg | Glu 415 | Ala |
| Glu | Arg | Ala | Asp 420 | Ala | Ala | Tyr | Cys | Arg 425 | Ala | Glu | Gln | Leu | Arg 430 | Ile | Ala |
| Gln | Glu | Ala 435 | Ala | Asp | Ala | Gln | Lys 440 | Ala | Phe | Ala | Glu | Ala 445 | Leu | Leu | Met |
| Pro | Gly 450 | Asn | Asn | Asp | Asn | Gly 455 | Gly | Asp | Asn | Ser | Ser 460 | Asp | Asp | Lys | Gly |
| Thr 465 | Gly | Ser | Ser | Asp | Ile 470 | Gly | Thr | Trp | Gly | Pro 475 | Phe | Ala | Ala | Ile | Ala 480 |
| Ala | Ile | Ile | Ala | Ala 485 | Ile | Ala | Ala | Ile | Phe 490 | Pro | Phe | Leu | Ser | Gly 495 | Ile |
| Gly | | | | | | | | | | | | | | | |

( 2 ) INFORMATION FOR SEQ ID NO:7:

( i ) SEQUENCE CHARACTERISTICS:
        ( A ) LENGTH: 2693 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:

(A) ORGANISM: Brevibacterium lactofermentum
(B) STRAIN: YSR (xi) SEQUENCE DESCRIPTION: SEQ ID NO:7:

| | | | | | | |
|---|---|---|---|---|---|---|
| ACTGGGAGGC | TATCTCCATT | GGGCGGTGCT | GTCATCGTTG | GCAGCTTTTC | CATCCTGGAT | 60 |
| GGGGTTCTGG | GCAGGACTGC | CTTTGGCGGT | CCTGTTAAAC | GTCGCGGTTT | GGTTGTACAC | 120 |
| CATCTATTCG | ATGGCAACCA | TGGATGAAGA | TGATGCGCGG | CTGCAAGGGG | AAACAGCTCC | 180 |
| GTCATACTTT | GAACGGATGC | TGTGGGTGTG | CAAAATTTCG | TTGTGGGGCA | TTGATTTTTG | 240 |
| GAAAAGTAT | CGCATCGCAT | TAGCGATGTC | TAAATCTTGG | CTGAAACCAT | TACATTTGCT | 300 |
| GTGTGCGAAC | TGTATATCAG | CTGATATTGC | GCCTAAATTC | CTGTGAATTA | GCTGATTTAG | 360 |
| TACTTTTCGG | AGGTGTCTAT | TCTTACCAAA | TTCGTCAAGT | TGTGGGTAGA | GTCACCTGAA | 420 |
| TATTAATTGC | ACCGCACCGG | GTGATATATG | CTTATTTGCC | TCAAGTAGTT | CGAGGTTAAG | 480 |
| TGTATTTTAG | GTGAACCAAA | TTTCAGCTTC | GGGTAGAAGA | CTTTCGATGC | GCTTCAGAGC | 540 |
| TTCTATTGGG | AAATCTGACA | CCACTTGATT | AAATAGCCTA | CCCCCGAATT | GGGGAGATTG | 600 |
| GTCATTTTTT | GCTGTGAAGG | TAGTTTTGAT | GCATATGACC | TGCCGTTTAT | AAAGAAATGT | 660 |
| AACGTGATCA | GATCGATATA | AAGAACAGTT | GTACTCAGGT | TTGAAGGCAT | TCTCCGATTC | 720 |
| GCTGGCAAAT | CTCATTGTCG | GCTTACAGTT | TTCTCAACGA | CAGGCGTGCT | AAGCTGCTAG | 780 |
| TTCAGGTGGC | CTAGTGAGTG | GCGTTTACTT | GGATAAAAGT | AATCCCATGT | CGTGATCAGC | 840 |
| CATTTGGGT | TGTTTCCATA | GCAATCCAAA | GGTTTCGTCT | TTCGATACCT | ATTCAAGGAG | 900 |
| CCTTCGCCTC | TATGTTAAC | AACCGTATCC | GGCACTGCAG | CTCTCGCATG | GTGCAATCGC | 960 |
| AATCTCCACC | GCAGCTTCCG | GCGTAGCTAT | CCCAGCATTC | GCTCAGGAGA | CCAACCCAAC | 1020 |
| CTTCAACATC | AACCAACGGC | TTCAACGATG | CTGATGGATC | CACCATCCAG | CCAGTTGAGC | 1080 |
| CAGTTAACCA | CACCGAGGAA | ACCCTCCGCG | ACCTGACTGA | CTCCACCGGC | GCTTACCTGG | 1140 |
| AAGAGTTCCA | GTACGGCAAC | GTTGAGGAAA | TCGTTGAAGC | ATACCTGCAG | GTTCAGGCTT | 1200 |
| CCGCAGACGG | ATTCCGGATC | CTTCTGAGCA | GGCTGCTTTA | CGAGGCTTTC | GAGGCTGCTC | 1260 |
| GCGTTCGTGC | ATCCCAGGAG | CTCGCGGCTT | CCGCTGAGAC | CATCACTAAG | ACCCGCGAGT | 1320 |
| CCGTTGCTTA | CGCACTCAAG | GCTGACCGCG | AAGCTACCGC | AGCTTTCGAG | GCTTACCTCA | 1380 |
| GCGCTCTTCG | TCAGGTTTCA | GTCATCAACG | ATCTGATCGC | TGATGCTAAC | GCCAAGAACA | 1440 |
| AGACTGACTT | TGCAGAGATC | GAGCTCTACG | ATGTCCTTTA | CACCGACGCG | GACATCTCTG | 1500 |
| GCGATGCTCC | ACTTCTTGCT | CCTGCATACA | AGGAGCTGAA | GGACCTTCAG | GTGCATACAA | 1560 |
| GGAGCTGAAG | GACCTTCAGG | CTGAGGTTGA | CGCAGACTTC | GAGTGGTTGG | GCGAGTTCGC | 1620 |
| AATTGATAAC | AATGAAGACA | ACTACGTCAT | TCGTACTCAC | ATCCCTGCTG | TAGAGGCACT | 1680 |
| CAAGGCACGC | GATCGATTCA | CTGGTCGACA | CCGTTGAGCC | ACTTCGTGCA | GACGCTATCG | 1740 |
| CTAAGAACAT | CGAGGCTCAG | AAGTCTGACG | TTCTGGTTCC | CCAGCTCTTC | TCGAGCGTGC | 1800 |
| AACTGCACAG | CGCGACACCC | TGCGTGTTGT | AGAGGCAATC | TTCTCTACCT | CTGCTCGTTA | 1860 |
| CGTTGAACTC | TACGAGAACG | TCGAGAACGT | TAACGTTGAG | AACAAGACCC | TTCGCCAGCA | 1920 |
| CTACTCTTCC | CTGATCCCTA | ACCTCTTCAT | CGCAGCGGTT | GGCAACATCA | ACGAGCTCAA | 1980 |
| CAATGCAGAT | CAGGCTGCAC | GTGAGCTCTT | CCTCGATTGG | GACACCGACC | TCACCACCAA | 2040 |
| CGATGAGGAC | GAAGCTTACT | ACCAGGCTAA | GCTCGACTTC | GCTATCGAGA | CCTACGCAAA | 2100 |
| GATCCTGATC | AACGGTGAAG | TTTGGCAGGA | GCCACTCGCT | TACGTCCAGA | ACCTGGATGC | 2160 |
| AGGCGCACGT | CAGGAAGCAG | CTGACCGCGA | AGCAGAGCGC | GCAGTGACGC | AGCATATTGC | 2220 |
| CGCGCTGAGC | AGCTCCGCAT | CGCTCAGGAA | GCAGCTGACG | CTCAGAAGGC | TCTTCGCTGA | 2280 |

| | | | | | | |
|---|---|---|---|---|---|---|
| GGCTCTGCTA | ATGCCAGGCA | ACAACGACAA | CGGTGGCGAC | AACTCCTCCG | ACGACAAGGG | 2340 |
| AACCGGTTCT | TCCGACATCG | GAACCTGGGG | ACCTTTCGCA | GCAATTGCAG | CTATCATCGC | 2400 |
| AGCAATCGCA | GCTATCTTTC | CCATTCCTCT | CCGGTATTCG | GTTAAGTTCT | AATTTCGAAC | 2460 |
| CGAGATAGCT | AAAAGTTAAA | CCACCTCCTT | TCCTTGGCCG | GGAGGTGGTT | TTTCCCTTGT | 2520 |
| TTAATTGCAC | TAAAAGAAAA | GCCACCTCCT | GCTTAAAGG | AGGTGGCTTT | TCTTCGTCTA | 2580 |
| CCTAGTTGAA | ATAGAGGTGG | GCGTCGATAA | GCAAAAATCT | TTTGCTTTTA | AGGGAACGTG | 2640 |
| ATAATCGGCT | TAATGACCTC | CCGCTGGCAG | AATCTGCAAA | GGCATCATTG | ATC | 2693 |

CORYNEFORM BACTERIA DEFICIENT IN A CELL SURFACE PROTEIN

TECHNICAL FIELD

The present invention concerns breeding of microorganisms useful for production of useful substances such as L-amino acids by fermentation processes and methods for producing useful substances such as L-amino acids by fermentation processes using the above-mentioned microorganisms. More specifically, it relates to a novel cell surface layer protein derived from *Brevibacterium lactofermentum*, a DNA segment containing a gene coding for the protein and an application use thereof.

BACKGROUND ART

Coryneform bacteria are microorganisms producing L-amino acids such as L-gtutamic acid or L-lysine in a great amount and breeding for them has been conducted with an aim of improving the productivity of L-amino acids. Various studies have been made and reported so far for breeding of amino acid-producing bacteria using gene manipulation technology (Biotechnology letters, 2 (1980) 525–530, Appln. Environ. Microbiol., 144 (1979) 181–190, Abstract of Lecture for the Meeting of the Society of Agricultural Chemistry of Japan (1981) 8). However, all of them have been directed to the improvement of the productivity of amino acid per cell by utilizing genes in amino acid biosynthetic systems as materials and enhancing them and not directed to the improvement of the productivity by analyzing the function of a cell surface structure.

By the way, when an amino acid is produced by a fermentation process, ion exchange chromatography has usually been conducted in the course of purifying a produced amino acid but, if bacterial cells remain in a fermentation medium, an ion exchange resin column is clogged when the fermentation medium is passed through the column and, accordingly, a step of removing the bacterial cells from the fermentation medium is necessary. The step is usually conducted by centrifugation, filtration or the like and it will be extremely useful industrially if such cell separating operation can be saved or simplified.

It has been known that microbial cells are precipitated in the medium due to aggregation or the like after cultivation depending on the kind of microorganisms and separation of the cells from a culture medium is extremely easy for such microorganisms. However, no Coryneform bacteria used in amino acid production, having such a property have yet been reported and a method of providing microbial cells with aggregating or precipitating property has not yet been known as well.

The published pamphlet of WO 93/03158 discloses a novel cell surface layer protein similar to a K-protein of the present invention, but this protein is clearly distinguished from the K-protein. Further, this publication discloses a protein expression-secretion system utilizing a signal peptides of the cell surface layer protein but it has not yet been known that such protein contributes to incorporation of nutrients of Coryneform bacteria and aggregating nature of bacterial cells.

Further, while Coryneform bacteria have been used industrially as L-amino acid-producing bacteria, it has been found recently that the bacteria are highly secretory and there has been an attempt of utilizing them for the production of different protein already put to practical use for Bacilli. The above-mentioned international publication WO 93/03158 also discloses a technology of such kind.

The subject to be dissolved by the present invention is to obtain a novel cell surface layer protein that contributes to the incorporation of nutrients of Coryneform bacteria and a gene thereof, and obtain a transformant obtained by amplification of the gene in the cell of Coryneform bacteria. The present invention also has a subject of using Coryneform bacteria having an activity to produce useful substances such as L-amino acids as a host for the transformant and improving the process for producing the useful substances such as L-amino acids by fermentation processes using the above-mentioned host bacteria, as well as obtaining Coryneform bacteria having a aggregating property, which is deficient in the novel cell surface layer protein, to simplify a process of amino acid production.

DISCLOSURE OF THE INVENTION

As a result of an earnest study, the present inventors have succeeded in obtaining a novel cell surface layer protein and a gene thereof which contribute to incorporation of a nutrient of bacteria and have accomplished the present invention.

Specifically, the present invention provides a novel cell surface layer protein derived from *Brevibacterium lactofermentum* having following two sequences, (1)Thr-Leu-Arg-Gln-His-Tyr-Ser-Ser-Leu-Ile-Pro-Asn-Leu-Phe-Ile-Ala-Ala-Val-Gly-Asn-Ile-Asn-Glu-Leu-Asn-Asn-Ala-Asp-Gln-Ala-Ala-Arg-Glu-Leu-Phe-Leu-Asp-Trp-Asp-Thr (SEQ ID NO: 1), and (2)Asn-Lys-Thr-Asp-Phe-Ala-Glu-Ile-Glu-Leu-Tyr-Asp-Val-Leu-Tyr-Thr-Asp-Ala-Asp-Ile-Ser-Gly-Asp-Ala-Pro-Leu-Leu-Ala-Pro-Ala-Tyr-Lys (SEQ ID NO: 2), in the molecule, and having a molecular weight of about 63,000 dalton, a DNA fragment containing a gene coding for the protein, a recombinant DNA obtained by ligating the DNA fragment with a vector capable of autonomous replication in a cell of Coryneform bacteria, a transformant obtained by introducing and amplifying the DNA fragment in the cell of Coryneform bacteria and a method for producing useful substances such as L-amino acid by fermentation processes which comprise culturing the transformant having an activity to produce useful substance such as L-amino acid in a culture medium, forming and accumulating the useful substance in the culture medium and collecting the useful substance from the culture medium.

The present invention provides Coryneform bacteria having a cell aggregating property and being deficient in the cell surface layer protein described above or a protein substantially identical with the above-mentioned protein being present in the cell surface of Coryneform bacteria.

The present invention also provides Coryneform bacteria having a cell aggregating property and being deficient in the cell surface layer protein, in which a gene coding for the cell surface layer protein or a gene coding for a protein which is substantially identical with the above-mentioned protein and is present in the cell surface of Coryneform bacteria is destroyed by homologous recombination of a DNA fragment containing at least a portion of a gene coding for the cell surface layer protein with a DNA sequence on a chromosome which is identical or homologous with the DNA fragment.

The present invention further provides a process for producing a useful substance, comprising:

cultivating Coryneform bacteria having an activity to produce useful substance such as L-amino acid;

forming and accumulating the useful substance in a culture medium and;

collecting the useful substance from the culture medium, wherein the Coryneform bacteria is deficient in the above-mentioned novel cell surface layer protein and has a cell aggregating property, and further comprising a step of standing still the culture medium after the completion of cultivation thereby precipitating the cells of Coryneform bacteria.

The Coryneform bacteria referred to in the present invention are, as described later, a group of microorganisms which are bacilliform, aerobic, gram positive, non-acid-fast and asporogenous (as defined in Bargeys Manual of Determinative Bacteriology, 8th edition, 599p (1974)). Specific microorganisms belonging to such Coryneform bacteria may also be referred to hereinafter simply as "Coryneform bacteria". Further, the Coryneform bacteria being deficient in the cell surface layer protein according to the present invention and the Coryneform bacteria in which a gene coding for the cell surface layer protein is destroyed may sometimes be referred to collectively as "K-protein-deficient strain".

1. Novel cell surface layer protein, gene, transformant thereof and a process of production of L-amino acid The novel cell surface layer protein in the present invention is obtained as described below. Cells of *Brevibacterium lactofermentum*, for example, strain 2256 (ATCC 13869) are disrupted, for example, using a supersonicator (OHTAKE 5202PZT), then the cell lysate is centrifuged under a condition stronger than the condition of 3,000× g for 5 min at 4° C., preferably, 12,000× g for 1 min at 4° C. to recover supernatant. Then, the supernatant is centrifuged under a condition stronger than the condition of 100,000× g for 20 min at 4° C., preferably, 100,000× g for 30 min at 4° C., and precipitates are recovered as a cell surface layer fraction. The protein present in a great amount around a molecular weight of 63,000 in this fraction is a novel cell surface layer protein according to the present invention, that is, the K-protein.

The K-protein is purified as described below. The prepared cell surface layer fraction contains both the cytoplasmic membrane and cell wall. Then, they are separated by solubilizing the cytoplasmic membrane using a surface active agent. Since the extent of solubilization differs depending, for example, on the kind and concentration of the surface active agent, time and temperature of the solubilization process and concentration of additional glycerol and/or NaCl, the present invention can be completed only when the optimum conditions for the purification are found. Determination for the optimum conditions has been established for the first time according to the present invention. That is, 3.0 µg of an cell surface layer fraction is added to 1 ml of a buffer solution (50 mM potassium phosphate, pH 8.0, 0.1 mM dithiothreitol) containing 1.25% (w/v) SDS, kept at 4 to 90° C., preferably, at 37° C. for more than 30 min, preferably, for one hour, then applied with centrifugation under a condition stronger than the condition of 145,000× g for 20 min, preferably, 145,000× g for 30 min and precipitates are recovered. The precipitates are suspended in 50 mM potassium phosphate at pH 8.0 containing 0.1% SDS such that the suspension contains 0.01–10 µg protein/µl, preferably, 0.2 µg protein/µl, and then solubilized by boiling for about 3 min.

The molecular weight of the K-protein is estimated from the mobility in SDS-polyacrylamide gel electrophoresis (Gel Electrophoresis of Proteins, IRL Press (1981) B. D. Hammes, et al). The molecular weight of the K-protein is estimated as about 63,000.

The amino acid sequence of the K-protein is determined as described below. The purified K-protein is suspended in 50 mM Tris-HCl, pH 7.3 containing 0.1% SDS such that the suspension contains of 10 µg protein/ml–2 mg protein/ml, preferably, 200 µg protein/ml and the suspesion is boiled for about 5 min to solubilize the K-protein. After allowing the solution to cool, the solution is added with endoproteinase Lys-C (manufactured by Boeringer Mannheim Co.) such that the ratio of the protein fraction insoluble in a surface active agent and Lys-C is about 10:1–200:1, preferably, 50:1 (wt/wt) and incubated at 37° C. for more than 30 min, preferably, at 37° C. for 3 hours.

The K-protein partialy digested with Lys-C is fractionated by reverse phase chromatography. Commercially available columns may be properly selected for the chromatography, for example, Senshu Pac VP-318-1251 4.6φ×250 mm can be used. Elution is carried out by using a gradient solution such as $CH_3CN$–0.1% TFA. The flow rate may be at 1 ml/min. Among thus obtained fractions, a fraction of higher peptide content is used to determine the amino acid sequence. The method of determination is according to a known method (P. Edman, Arch. Biochem. 22 475 (1949)), for example, by using a Gas Phase Sequencer 470-A manufactured by Applied Biosystems Co. and in accordance with the supplier's manual.

The K-protein has the following two sequences in the molecule:

(1) Thr-Leu-Arg-Gln-His-Tyr-Ser-Ser-Leu-Ile-Pro-Asn-Leu-Phe-Ile-Ala-Ala-Val-Gly-Asn-Ile-Asn-Glu-Leu-Asn-Asn-Ala-Asp-Gln-Ala-Ala-Arg-Glu-Leu-Phe-Leu-Asp-Trp-Asp-Thr (sequence table, SEQ ID No:1) and (2) Asn-Lys-Thr-Asp-Phe-Ala-Glu-Ile-Glu-Leu-Tyr-Asp-Val-Leu-Tyr-Thr-Asp-Ala-Asp-Ile-Ser-Gly-Asp-Ala-Pro-Leu-Leu-Ala-Pro-Ala-Tyr-Lys (sequence table, SEQ ID No:2).

K-protein gene is isolated as follows. Chromosomal DNA is at first extracted from *Brevibacterium lactofermentum*, for example, strain 2256 (ATCC 13869) (a method for example described by H. Saito and K. Miura, in Biochem. Biophys. Acta 72, 610 (1963) can be used), and digested with an appropriate restriction enzyme. A wide variety of restriction enzymes can be used if the extent of digestion of the chromosomal DNA is controlled by regulation of the reaction conditions, for example reaction time.

The DNA fragment and a vector DNA capable of replicating in the cell of a microorganism belonging to the genus Escherichia are ligated to form a recombinant DNA, and then the Escherichia bacteria, for example, *Escherichia coli* strain JM109 is transformed with the recombinant DNA to prepare a genomic DNA library. The K-protein gene can be isolated from the library by colony hybridization using a synthetic DNA having a nucleotide sequence deduced from a known amino acid sequence as a probe.

Specifically, chromosomal DNA of *Brevibacterium lactofermentum*, strain 2256 (ATCC 13869) is partially digested with a restriction enzyme, for example, Sau3AI at a temperature higher than 30° C., preferably, 37° C. at an enzyme concentration of 1 to 10 unit/ml for various times (1 min to 2 hours), to obtain mixtures of various size of chromosomal DNA fragments. The vector DNA capable of replicating in the cells of Escherichia bacteria is completely cleaved with a restriction enzyme causing an identical terminal base sequence with that of the restriction enzyme Sau3AI used for digesting the chromosomal DNA, for example, BamHI, at a temperature higher than 30° C. and an enzyme concentration of 1 to 100 unit/ml for more than one hour, preferably, for 1 to 3 hours to obtain cleaved and linearized DNA. Then, the mixture containing the DNA fragment including the K-protein gene derived from *Brevibacterium lactofermentum* strain 2256 (ATCC 13869) obtained as described above and the linearized vector DNA are mixed and ligated using DNA ligase, preferably, T4 DNA ligase at a temperature of 4° to 16° C., an enzyme concentration of 1 to 100 units, for more than one hour, preferably, 6 to 24 hours to obtain a recombinant DNA.

As the vector DNA that can be used in the present invention, a plasmid vector DNA is preferred and there can be mentioned, for example, pUC19, pUC18, pBR322, pHSG299, pHSG399 and RSF1010. In addition, a phage DNA vector can also be used. For efficiently expressing the K-protein gene, a promotor operating in microorganisms such as lac, trp, PL may also be used. The recombinant DNA referred to herein may include a recombinant DNA obtained by integrating the K-protein gene into chromosome by a method of using transposon (Berg. D. E. and Berg. C. M. Bio/Technol., 1 417 (1983)), Mu phage (Japanese Patent Laid-Open Publication 90-109985) or by homologous recombination (Experiments in Molecular Genetics, Cold Spring Harbor Lab. (1972)).

A gene library is prepared by transforming, for example, *Escherichia coli* K-12, preferably, JM109 with the above-mentioned recombinant DNA. A method of preparing the gene library is detailed in Molecular Cloning second edition (Cold Spring Harbor Press (1989) Maniatis, et al.). Transformation can be performed by the method of D. M. Morrison (Methods in Enzymology 68, 326, 1979) or a method of enhancing DNA permeability by treating recipient cells with calcium chloride (Mandel, M. and Higa, A., J. Mol. Biol., 53, .159 (1970)).

Successively, a recombinant DNA containing a DNA fragment that includes the K-protein gene is isolated from the gene library by a colony hybridization method. The colony hybridization can be performed in accordance with the method as described in Molecular Cloning second edition (Cold Spring harbor Press (1989) Maniatis, et al.).

As a DNA probe used in the colony hybridization, a synthetic DNA having a base sequence deduced from the amino acid sequence of the purified K-protein is used. For example, a 30 mer oligonucleotide having a sequence of 5'-TTCATCGCTGCTGTCGGCAACATCAACGAG-3' (SEQ ID No:3) synthesized by using a DNA Synthesizer manufactured by Applied Biosystems Co. can be mentioned preferably. Upon determination of the sequence, presence of a plurality of codons corresponding to a kind of amino acid residue results in a remarkable hindrance. In view of the above, the sequence is determined by selecting a region in which the degree of degeneracy of the codons corresponding to each amino acid is low or by referring to the codon usage of the genus Brevibacterium. Oligonucleotide can be synthesized in accordance with a customary manner by using a DNA Synthesizer Model 380B manufactured by Applied Biosystems Co. and using a phosphoamidide method (refer to Tetrahedron Letters, 22, 1859 (1981)).

Alternatively, the K-protein gene can also be obtained by amplifying the K-protein genes from the chromosomal DNA obtained, for example, by a method of H. Saito and K. Miura Biochem. Biophys. Acta. 72, 619 (1963) by PCR (polymerase chain reaction: White, T. J. et al: Trends Genet, 5, 185 (1989). DNA primers used for PCR are complementary to sequences of both 3' termini of double-stranded DNA including a whole or a partial region of the K-protein gene. In a case of amplifying only a partial region of the K-protein gene, it is necessary to screen the DNA fragment including the whole K-protein gene from the gene library by using the above-mentioned DNA fragment as a probe. In a case of amplifying the whole gene, DNA fragments including the K-protein gene can be recovered by separation of PCR reaction mixture by agarose gel electrophoresis and then cutting out a band containing the desired DNA fragment from an agarose gel.

As the DNA primer, a synthetic DNA having a base sequence deduced from the purified K-protein amino acid sequence is used. Upon determination of the sequence, presence of a plurality of codons corresponding to a kind of amino acid residue results in a remarkable hindrance. In view of the above, the sequence is determined by selecting a region in which the degree of degeneracy of the codons corresponding to each amino acid is low or by referring to the codon usage of the genus Brevibacterium. The DNA can be synthesized in accordance with a customary method by using a DNA Synthesizer Model 380B manufactured by Applied by Biosystem Co. and using the phosphoamidide method. The PCR reaction can be conducted by using DNA Thermal Cycler Model PJ2000 manufactured by Takara Shuzo Co., using a Taq DNA polymerase and in accordance with a method designated by the supplier.

The DNA fragment containing the whole K-protein gene or a partial region of the K-protein gene amplified by the PCR reaction is ligated to a vector DNA capable of replicating in cells of bacteria belonging to the genus Escherichia to form a recombinant DNA. Then the recombinant DNA is introduced into the cell of bacteria belonging to the genus Escherichia. The vector DNA and the transforming method used herein are identical as those described previously. In a case of amplifying only a partial region of the K-protein gene, a DNA fragment containing the whole K-protein gene can be isolated from the gene library by using the above-mentioned DNA· fragment as a probe. As the isolation method, the colony hybridization method described previously may be used.

Whether the isolated DNA fragment containing the K-protein gene actually contains the K-protein gene or not is confirmed by nucleotide sequencing of the DNA fragment using the synthetic DNA used for colony hybridization or PCR as a primer and by confirming if the determined nucleotide sequence codes for the above-mentioned amino acid sequence. The nucleotide sequence can be determined by a dideoxy method (Molecular Cloning second edition (Cold Spring Harbor Press (1989), Maniatis et al)).

Whether the K-protein is the novel cell surface layer protein contributing to the incorporation of nutrients of Coryneform bacteria or not can be confirmed by preparing K-protein-deficient strain and measuring the activity of the K-protein-deficient strain to incorporate ammonium ions. Then, it is confirmed that the numerical value shows remarkable reduction as compared with the ammonium ion incorporating activity of a K-protein sufficient strain.

Then, explanation will be made to a recombinant DNA obtained by ligating the DNA fragment containing the K-protein gene with a vector capable of autonomous replication in the cells of Coryneform bacteria, a transformant of Coryneform bacteria obtained by introduction and amplification of the DNA fragment in the cell and a process for producing L-amino acid by a fermentation process which comprises cultivating the above-mentioned transformant having L-amino acid productivity, forming and accumulating L-amino acid in a culture medium and collecting the L-amino acid from the culture medium.

The Coryneform bacteria referred to in the present invention, for example, microorganisms belonging to Brevibacterium or Corynebacterium are a group of microorganisms defined in Bargeys Manual of Determinative Bacteriology (8th edition, p 599, (1974)), which are bacilliform, aerobic, gram positive, non-acid-fast and asporogenous. Among the microorganisms of Brevibacterium or Corynebacterium, L-glutamic acid producing bacteria belonging to the genus Brevibacterium or the genus Corynebacterium described below can be used in the present invention.

As examples of wild type strains of glutamic acid producing bacteria belonging to the genus Brevibacterium or the genus Corynebacterium, there can be mentioned the followings.

| | |
|---|---|
| Brevibacterium dibaricatum | ATCC 14020 |
| Brevibacterium saccharoriticum | ATCC 14066 |
| Brevibacterium immariofilm | ATCC 14068 |
| Brevibacterium lactofermentum | ATCC 13869 |
| Brevibacterium roseum | ATCC 13825 |
| Brevibacterium flabum | ATCC 13826 |
| Brevibacterium thiogenetallis | ATCC 19240 |
| Brevibacterium acetoacidfilum | ATCC 13870 |
| Brevibacterium acetoglutamicum | ATCC 15806 |
| Brevibacterium calnae | ATCC 15991 |
| Corynebacterium glutamicum | ATCC 13032, 13060 |
| Corynebacterium lilyum | ATCC 15990 |
| Corynebacterium meracecola | ATCC 17965 |
| Microbacterium ammoniafilum | ATCC 15354 |

Any vector DNA that can replicate in the bacterial cells of Brevibacterium or Corynebacterium can be used in the present invention. There can be specifically exemplified the followings.

(1) pAM 330 refer to Japanese Patent Laid-Open Publication 83-67699

(2) pHM 1519 refer to Japanese Patent Laid-Open Publication 83-77895

(3) pAJ 655 refer to Japanese Patent Laid-Open Publication 83-192900

(4) pAJ 611 ditto (5) pAJ 1844 ditto (6) pCG 1 refer to Japanese Patent Laid-Open Publication 82-134500

(7) pCG 2 refer to Japanese Patent Laid-Open Publication 83-35197

(8) pCG 4 refer to Japanese Patent Laid-Open Publication 82-183799

(9) pCG 11 ditto

The vector DNA is cleaved with a restriction enzyme that cleaves the vector DNA at a unique site, or by partially cleavage with a restriction enzyme that cleaves the DNA at a plurality of its recognition sites.

The vector DNA is cleaved with the restriction enzyme used for cleavage of the DNA fragment that codes for the K-protein gene and ligated with the DNA fragment. If the vector DNA is cleaved with a restriction enzyme which forms different termini from that of the DNA fragment that codes for the K-protein gene, oligonucleotide linkers having base sequence complementary to termini of the linearized vector are ligated to both termini of the DNA fragment, and then the linker-tailed DNA fragment is ligated with the vector DNA.

Resulting recombinant DNA in which the vector DNA and the DNA fragment that codes for the K-protein gene are ligated can be introduced into recipients belonging to the genus Brevibacterium or the genus Corynebacterium, by a method of enhancing the DNA permeability by treating the recipient cells with calcium chloride as reported for *Escherichia coli* K-12 (Mandel, M. and Higa, A., J. Mol., Biol., 53 159 (1970), or a method of introducing DNA into a exponential stage of cells such that cells can incorporate the DNA (so-called competent cell) as reported for *Bacillus subtilis* (Duncan, C. H., Wilson, G. A. and Young, F. E., Gene, 1 153 (1977)). Alternatively, the recombinant DNA can also be introduced into bacterial cells by converting the cells into protoplasts or spheroplasts capable of readily incorporating the recombinant DNA as known for *Bacillus subtilis*, Actinomycetes and yeasts (Chang, S. and Choen, S. N., Molec. Gen., Genet., 168 111 (1979); Bibb, M. J., Ward, J. M. and Hopwood, O. A., Nature, 274, 398 (1978); Hinnen, A., Hicks, J. B. and Fink, G. R. Proc. Natl. Acad. Sci. USA, 75, 1929 (1978)).

In the protoplast method, a sufficiently high frequency of transformation can be obtained also by a method used for *Bacillus subtilis* described above, and a method of incorporating the DNA into the protoplast of Corynebacterium or Brevibacterium under the presence of polyethylene glycol or polyvinyl alcohol and divalent metal ions disclosed by Japanese Patent Laid-Open Publication 82-183799 can of course be utilized. Similar results can also be obtained by a method of promoting the incorporation of the DNA, for example, by addition of carboxymethyl cellulose, dextran, ficoll or Bulronic F68 (manufactured by Selba Co.) instead of polyethylene glycol or polyvinyl alcohol.

Further, the recombinant DNA can be introduced into the recipient bacteria belonging to the genus Brevibacterium or the genus Corynebacterium by an electric pulse method (also called electroporation) (Sugimoto, et al., Japanese Patent Laid-Open Publication 90-207791).

L-amino acid producing transformant obtained by the method described above, which harbors the recombinant DNA containing the DNA fragment that codes for the K-protein is cultivated and a desired L-amino acid is produced and accumulated in a culture medium, which is then collected.

The culture medium for L-amino acid production used herein is a usual culture medium containing a carbon source, nitrogen source, inorganic ions and if necessary, other organic ingredients.

As the carbon source, saccharides such as glucose, lactose, galactose, fructose or hydrolyzates of starch. alcohols such as glycerol or sorbitol, and organic acid such as fumaric acid, citric acid and succinic acid can be used.

As the nitrogen source, inorganic ammonium salts such as ammonium sulfate, ammonium chloride and ammonium phosphate, organic nitrogen such as hydrolyzates of soybean, gaseous ammonia and ammonium hydroxide can be used.

As the organic micro-nutrients, culture medium is desirable to be added with required substances such as vitamin B1 or yeast extract in appropriate amount. In addition, a small amount of potassium phosphate, magnesium sulfate, iron ions, manganese ions, etc. is added if necessary.

Cultivation is preferably carried out under an aerobic condition for 16 to 72 hours, while controlling cultivation temperature at 30° C. to 45° C. and pH at 5 to 7 during cultivation. Inorganic or organic acidic or alkaline substance and, further, gaseous ammonia etc. can be used for pH adjustment. L-amino acid can be collected from the fermentation liquid by a combination of usual ion exchange resin method, precipitation method and other known method.

By the way, Coryneform bacteria are microorganisms producing L-amino acids in a great amount and have been utilized generally for the production of L-amino acids by the fermentation process. In addition, high secreting property of the Coryneform bacteria have also been utilized for the production of various materials.

Since it is considered that the K-protein is present in the cell surface layer and contributes to the incorporation of nutrients into cytoplasm, if a transformant of Coryneform bacteria obtained by the introduction and replication of DNA fragments containing the K-protein gene in the cell has a useful substance productivity, it is considered that a process for producing useful substance by the fermentation process which comprises cultivating the transformant in a culture medium, forming and accumulating the useful substance in the culture medium and collecting the useful substance from the culture medium also can be improved.

The main part of the process for producing the useful substance, which comprises cultivating the transformant in the culture medium, forming and accumulating the useful substance in the culture medium and collecting the useful substance from the culture medium, is identical with the process for producing amino acids described above.

The useful substance referred to herein includes nucleic acids as a raw material for seasonings. The Coryneform bacteria producing nucleic acids include, for example, *Corynebacterium equi* AJ 11347 as disclosed in Japanese Patent Publication 82-22558.

On the other hand, the useful substance includes foreign proteins. Namely, there can be mentioned physiologically active substances such as human interferon, human interleukin or human hormone, enzyme or antibody. Methods of producing foreign proteins by using microorganisms have been known mainly for bacteria of Escherichia or Bacillus, and a similar technique has also been developed for Coryneform bacteria. The technique basically comprises preparing a recombinant DNA by ligating a vector capable of autonomous replication in the cells of Coryneform bacteria with a promotor that can operate in the cells of Coryneform bacteria and a DNA fragment that codes for the foreign protein, introducing the recombinant DNA into the Coryneform bacteria and producing the protein through expression of the DNA that codes for the protein on the recombinant DNA. The technology is disclosed, for example, in Japanese Patent Laid-Open Pablication 87-151184 or Japanese Patent Laid-Open Publication 87-244382.

(2) K-protein-deficient strain and a process for producing L-amino acid utilizinq them As described above, it has been confirmed that the K-protein found for the first time according to the present invention contributes to the incorporation of nutrients of the Coryneform bacteria and it is further disclosed by the present invention that the Coryneform bacteria also contribute to aggregating property of bacterial cells and Coryneform bacteria which is deficient in the K-protein exhibit aggregating nature.

The K-protein-deficient strain are obtained by causing such a mutation as not substantially producing the K-protein to the K-protein gene, for example of *Brevibacterium lactofermentum*. Alternatively, a spontaneous mutant strain having such a mutation as not substantially producing the K-protein may be selected from the natural world.

Further, the K-protein-deficient strain can also be obtained by destroying the K-protein gene by homologous recombination between a DNA fragment containing at least a portion of a gene that codes for the K-protein and the K-protein gene on the chromosome.

Further, it is anticipated that even Coryneform bacteria other than *Brevibacterium lactofermentum* have a protein identical with or substantially identical with the K-protein (hereinafter referred to as a "K-protein-like protein") in cell surface layer. For instance, the published pumphlet of WO 93/03158 describes a novel cell surface layer protein which is similar to but can be distinguished clearly from the K-protein of the present invention.

It is expected that such a K-protein-like protein also contributes to the incorporation of nutrients or to the aggregating property of bacterial cells and the Coryneform bacteria being deficient in the K-protein-like protein also have a aggregating property.

The Coryneform bacteria being deficient in the K-protein-like protein can be obtained, in the same manner as the K-protein-deficient strain, by causing such mutation as not substantially producing the K-protein-like protein to the K-protein-like protein gene. Further, a spontaneous mutant strain having such mutation as not substantially producing the K-protein-like protein may be selected from the natural world. Further, Coryneform bacteria being deficient in the K-protein-like protein can also be obtained by destroying the gene coding for the K-protein-like protein by homologous recombination between a DNA fragment containing at least a portion of a K-protein gene and a gene coding for K-protein-like protein on the chromosome which is homologous with the DNA fragment.

Description will now be made to a method of obtaining the K-protein-deficient strain. In the following descriptions, if the K-protein is replaced with the K-protein-like protein, the strain being deficient in the K-protein-like protein can be obtained also in the same manner.

Mutations not substantially producing the K-protein can be caused to the K-protein gene by applying a usual method of causing artificial mutation to microorganisms such as UV irradiation or by a treatment with a mutagenic agent such as N-methyl-N'-nitro-N-nitrosoguanidine (NTG).

As a method of selecting the K-protein-deficient strain from the Coryneform bacteria subjected to mutagenization, there can be mentioned, for example, a method using an anti-K-protein antibody, for instance, a Western blotting method. More specifically, colonies of mutagenized Coryneform bacteria are formed on a membrane such as a nylon membrane placed on an agar medium plate to fix the cellular protein on the membrane. In this case, a replica plate is prepared on a separate agar medium plate such that 1:1 correspondence is obtained with the colonies on the membrane. Then, when the membrane is immersed successively into solutions containing an anti-K-protein antibody, an enzyme-labelled second antibody against an immunoglobulin fraction of immunized animal used for preparation of the anti-K-protein antibody, and dyes that develops color through an enzymatic reaction caused by the labeling enzyme, respectively, and then incubated, a color is developed at a position to which the cell protein of the K-protein sufficient bacteria is fixed. Accordingly, the K-protein deficient bacteria can be selected by identifying the colony not causing the color development of the dye and isolating the colony from the replica plate corresponding to this colony. It is preferred that SDS-polyacrylamide gel electrophoresis is carried out for proteins of the cell surface layer fraction of thus selected K-protein-deficient strain to confirm that K-protein is not substantially expressed.

The anti-K-protein antibody is obtained by immunizing an animal such as mouse by using the K-protein prepared from the cell surface layer fraction of *Brevibacterium lactofermentum* as shown in (1) above, in the same manner as a usual preparation method for immunization and collecting blood. It is also possible to use an anti-K-protein monoclonal antibody obtained by fusing spleen cells of an animal immunized by the K-protein and culture cells having a continuous growing activity such as a mouse myeloma cell to prepare hybridoma cells and cultivating them.

The enzyme-labelled second antibody is obtained by forming a covalent bond between an enzyme such as β-galactosidase or horseradish peroxidase and an anti-immunoglobin antibody against an immunoglobulin fraction of an immunized animal used for the preparation of the anti-K-protein antibody. Enzyme-labeled antibodies against immunoglobulins from various animals are commercially available and usable.

Another method of selecting K-protein-deficient strain from mutagenized Coryneform bacteria will be explained. A cell surface layer fraction is prepared by the method as described in (1) above for cells put to single colony isolation and cell surface layer fractions are obtained and subjected to SDS-polyacrylamide gel electrophoresis. A strain for which no K-protein band is detected near the molecular weight of about 63,000 is the K-protein-deficient strain. Although the method is extremely time-consuming, it is desirable to adopt it for the secondary screening step since it can reliably select the K-protein-deficient strain.

By the same method as described above, a mutant strain having a mutation not substantially producing the K-protein can be selected from the natural world.

Then, explanation will be made to a method of obtaining the K-protein-deficient strain or K-protein-like protein-deficient strain by gene disruption. A DNA containing a DNA fragment that contains a portion of the K-protein gene is introduced into the cell of Coryneform bacteria, and homologous recombination is caused between the DNA fragment containing a portion of the K-protein gene and a DNA sequence on a chromosome which is identical or homologous with the DNA fragment, thereby interrupting the K-protein gene or the K-protein-like protein gene on the chromosomal DNA. A schematic view for the mechanism of the gene disruption is shown in FIG. 1.

More specifically, a DNA fragment containing a portion of the K-protein gene is ligated with a vector plasmid DNA, to prepare a plasmid for gene disruption. The plasmid for gene disruption is introduced into Coryneform bacteria such as Brevibacterium lactofermentum to obtain a transformant by a method of enhancing the DNA permeability by treating recipient cells with calcium chloride as reported for Escherichia K-12 (Mandel, M. and Higa, A., J. Mol., Biol., 53, 159 (1970), a method of introducing DNA into the growing stage of cells such that cells can incorporate DNA as reported for Bacillus subtilis (so-called competent cell) (Duncan, C. H., Wilson, G. A. and Young, F. E., Gene, 1, 153 (1977)), a method of converting the DNA recipient into protoplasts or spheroplasts capable of easily incorporating DNA and introducing the recombinant plasmid into the DNA recipient as known for Bacillus subtilis, Actinomycetes and yeasts (Chang, S. and Choen, S. N., Molec. Gen., Genet., 168, 111 (1979), Bibb, M. J., Ward, J. M. and Hopwood, O. A., Nature, 274, 398 (1978); Hinnen, A. Hicks, J. B. and Fink, G. R. Proc. Natl. Acad. Sci. USA, 75, 1929 (1978)), or a electric pulse method (Sugimoto, et al., Japanese Patent Laid-Open Publication 90-207791) in the same manner as (1) described above.

For a vector plasmid used for the preparation of the plasmid for gene disruption, it is preferred to use a vector having a temperature sensitive replication origin, for example, pHSC4 (Sugimoto, et al., French Patent Laid-Open Publication No. 2667875/1992) and the resulting transformant is cultivated at a replication inhibiting temperature. This can prevent the plasmid from autonomous replication outside the chromosome in the cell and make the transformant in which the plasmid is incorporated into the chromosome DNA able to grow preferentially. Further, for facilitating the selection of the transformant, it is desirable to use a vector plasmid possessing a marker gene, for example, a drug resistant gene.

When the Coryneform bacteria to which the plasmid for gene distruption is introduced is cultivated in a culture medium containing drug corresponding to the marker gene, preferably, at a replication-inhibitory-temperature, only a transformant in which the plasmid is integrated into the chromosome can grow. In such a transformant cell, the plasmid for gene destruction is integrated into the K-protein gene on the chromosome by homologous recombination between the DNA fragment containing a portion of the K-protein gene present in the plasmid for gene destruction and the K-protein gene or the K-protein-like protein gene on the chromosome and, as a result, the chromosomal K-protein gene is probably disrupted. Whether transformants thus obtained are deficient in the K-protein or not can be confirmed by subjecting the cell surface layer fraction of the transformant to polyacrylamide gel electrophoresis. Further, it can also be confirmed by the required aggregating nature of the transformant cells.

Included as Coryneform bacteria to be mutagenized to obtain the K-protein-deficient strain or to be disrupted with the K-protein gene are microorganisms of Brevibacterium or Corynebacterium as stated in (1) above.

Then, a description will be made to a process for producing L-amino acid, comprising: cultivating Coryneform bacteria having an activity to produce L-amino acid, forming and accumulating L-amino acid in the culture medium and collecting the L-amino acid from the culture medium, wherein the Coryneform bacteria are deficient in the K-protein or K-protein-like protein, and further comprising a step of standing still the culture medium after the completion of cultivation and thereby precipitating the cells of Coryneform bacteria.

Coryneform bacteria having an activity to produce the L-amino acid and being deficient the K-protein or K-protein-like protein are cultivated and a desired L-amino acid is formed and accumulated in the culture medium. The culture medium used for the production of the L-amino acid is a usual culture medium containing a carbon source, a nitrogen source, inorganic ions and, if necessary, other organic ingredients.

As the carbon source, there can be used, for example, saccharides such as beet molasses, cane molasses, glucose, sucrose, lactose, galactose, fructose and hydrolysates of starch, alcohols such as glycerol and sorbitol, and organic acids such as fumaric acid, citric acid and succinic acid.

As the nitrogen source, there can be used, for example, inorganic ammonium salts such as ammonium sulfate, ammonium chloride, ammonium phosphate, organic nitrogen such as hydrolysates of soybean, gaseous ammonia and ammonia hydroxide.

As the organic micro-nutrient source, it is desirable to add an appropriate amount of required substances such as vitamin B1 or yeast extract. In addition, small amounts of potassium phosphate, magnesium sulfate, iron ions and manganese ions are added to the culture medium as required.

Cultivation is preferably carried out under aerobic conditions for 16 to 72 hours while controlling the cultivation temperature at 30° C. to 45° C. and pH value at 5 to 7 during cultivation. For pH control, organic or inorganic acidic or alkaline substances and additional gaseous ammonia may be used.

Since the culture medium composition and cultivation conditions may give effects on the aggregating property of bacterial cells, conditions suitable for obtaining a K-protein-deficient strain may be properly selected.

Then, after completion of cultivation, the culture medium is allowed to stand and aggregated bacterial cells are precipitated to be separated from the supernatant. The supernatant and the bacterial cells can be separated by recovering the supernatant such that the precipitated bacterial cells are not included. Further, cell separation processes may be carried out by means of ordinary centrifugal separation or filtration, such processes being facilitated since the bacterial cells are aggregated.

After separation of the bacterial cells, the L-amino acid can be collected from the fermentation medium by a combination of customary ion exchange chromatography, precipitation and other known methods. A basic amino acid such as L-lysine is usually purified by a cationic exchange chromatography after adjusting the pH value of the fermentation solution to about 4. Since the K-protein-deficient strain according to the present invention further increases the aggregating property at a pH value of about 4, if the cell precipitating step is carried out after pH adjustment, precipitation can be completed in a shorter period of time thereby enabling more efficient separation of bacterial cells. Furthermore, supernatants separated from the bacterial cells can be passed as they are through the ion exchange resin column.

The present invention shows that the K-protein contributes to the aggregating property of the cells, and this concept is applicable also to a cell removal step downstream in fermentation industries other than production of L-amino acids, to a cell recycle type bioreactor and, further, to the improvement of the precipitation of active sludge bacteria, even in the fermentation industry other than that of L-amino acid.

For instance, when Coryneform bacteria which have an activity to produce a useful substance are deficient in the K-protein or K-protein-like protein and have a cell aggregating property, this enables the improvement of the process for producing a useful substance by a fermentation process which comprises cultivating the bacteria in a culture medium, forming and accumulating the useful substance in the culture medium and collecting the useful substance from the culture medium. This is due to the cell separating operation being essential in these production processes.

That is, cell separation is facilitated in the same manner as the amino acid production process described above in a process for producing a useful substance by a fermentation process comprising cultivating Coryneform bacteria having an activity to produce the useful substance, forming and accumulating the useful substance in a culture medium and collecting the useful substance from the culture medium, wherein the Coryneform bacteria is deficient the K-protein or K-protein-like protein and has a cell aggregating property, and further comprising a step of standing still the culture medium after the completion of cultivation thereby precipitating cells of the Coryneform bacteria.

The useful substance referred to herein includes nucleic acids as a raw material for seasonings. The Coryneform bacteria producing the nucleic acids includes, for example, *Corynebacterium equi* AJ 11347 as disclosed in Japanese Patent Publication 82-22558.

Further, the useful substance also includes foreign proteins. That is, there can be mentioned physiologically active substances such as human interferon or human interleukin, enzyme or antibody. Methods of producing foreign proteins using microorganisms have been known mainly for bacteria belonging to the genus Escherichia or the genus Bacillus and similar technology has been developed also for Coryneform bacteria. These techniques basically comprise ligating a vector capable of autonomous replication in the cell of Coryneform bacteria with a promotor that can operate in the cell of the Coryneform bacteria and DNA coding for a foreign protein to form a recombinant DNA, introducing the recombinant DNA into the Coryneform bacteria and producing the protein through the expression of DNA coding for the protein. This technique is disclosed for example in Japanese Patent Laid-Open Publication 87-151184.

The symbols shown above are also used for FIGS. 4 to 6.

Figure 4:
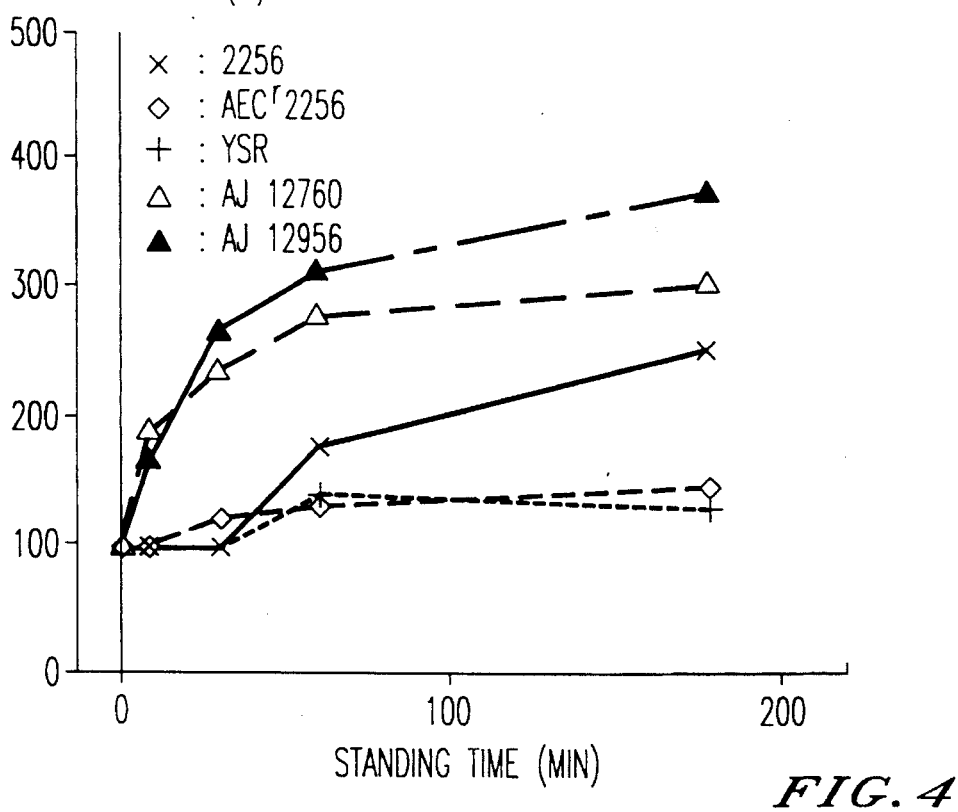

FIG. 4: diagram showing precipitation of K-protein-deficient and K-protein-sufficient strains (Carbon source: sucrose, culture medium after completion of cultivation adjusted to pH 4.0).

Figure 5:
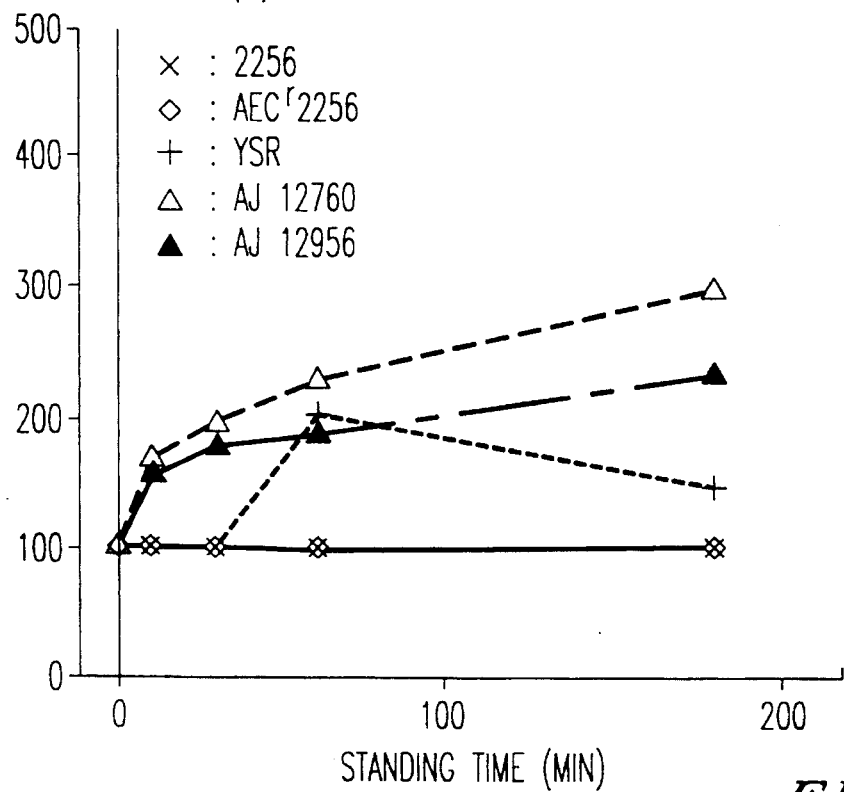

FIG. 5: diagram showing precipitation of K-protein-deficient and K-protein-sufficient strains (Carbon source: glucose, culture medium after completion of cultivation not adjusted for pH).

Figure 6:
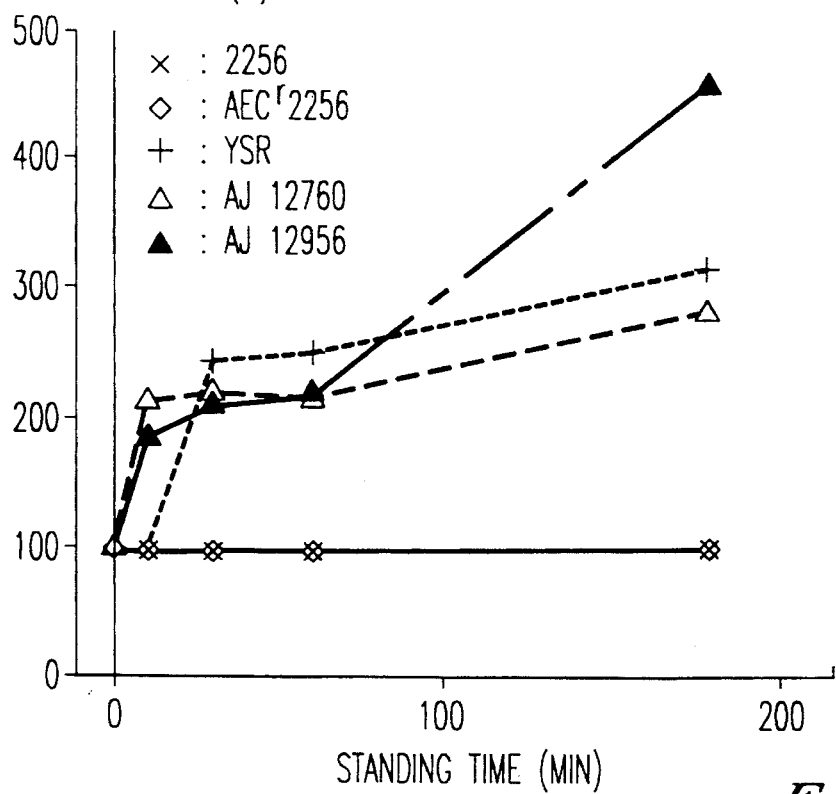

FIG. 6: diagram showing precipitation of K-protein-deficient and K-protein-sufficient strains (Carbon source: sucrose, culture medium after completion of cultivation not adjusted for pH).

BEST MODE FOR PRACTICING THE INVENTION

The present invention will now be described more concretely by way of examples.

EXAMPLE 1

Novel cell surface layer protein K-protein (1) Finding of novel cell surface layer protein

*Brevibacterium lactofermentum* ATCC 13869 was put to shaking cultivation over night at 30° C. in a CM2G culture medium (yeast extract 10 g, bacto tryptone 10 g, glucose 5 g, NaCl 5 g; filled up with water to 1 liter) and cells were collected from 1 ml of a culture both. After washing with a buffer solution A (50 mM potassium phosphate, pH 8.0, 10 mM magnesium sulfate), the cells were suspended in 1 ml of a buffer solution A, frozen and melted, and cells were broken by a supersonicator (OHTAKE 5202PZT) while kept at 0° C. Then, the cell lyzate was centrifuged at 12,000× g for 1 min at 4° C. and supernatant was recovered. Obtained supernatant was re-centrifuged at 100,000×g for 30 min at 4° C. and precipitates were recovered as cell surface layer fractions. Among the fractions, a portion corresponding to 5×10$^9$ cells was subjected to SDS-polyacrylamide gel electrophoresis. As a result, a protein band present in a great amount was found near the molecular weight of about 63,000 and this protein was named as K-protein.

The present inventors expected that the cell surface layer protein has a function to contribute to the incorporation of nutrients from the outside of the bacterial cell and proceeded the following experiments.

(2) Purification of K-protein At first, a cell surface layer fraction was prepared by the method as described previously in (1). The cell surface layer fraction contained both cytoplasmic membranes and cell walls. Then, it was attempted to separate them by solubilizing the cytoplasmic membranes using a surface active agent. As a result of detailed studies for the kind and the concentration of the surface active agent, the time and the temperature for solubilization, the effect of adding glycerol and the effect of adding NaCl, the K-protein could be purified by the method to be described below. Three μg of a cell surface layer fraction of the protein (quantification is performed by the BC protein assay kit manufactured by Bio Rad Co.) was suspended into 1 ml of a buffer solution containing 1.25% (w/v) SDS (50 mM potassium phosphate, pH 8, 0.1 mM dithiothreitol) and the suspension was kept at 37° C. for one hour. Then the suspension was centrifuged at 145,000×g for 30 min followed by recovering the precipitate. The precipitate was suspended in 50 mM potassium phosphate at pH 8.0, containing 0.1% SDS to 0.2 μg protein/μl, and boiled for 3 min. Fifteen μg of the protein as the surface active agent-insoluble fraction was subjected to SDS-polyacrylamide gel electrophoresis and it was confirmed that this is a homogeneous protein having a molecular weight of 63,000.

(3) Property of K-protein (3-1) Molecular weight

The molecular weight of the K-protein was estimated to about 63,000 based on the mobility in SDS-polyacrylamide gel electrophoresis.

(3-2) Determination of partial amino acid sequence

The K-protein purified by the method as described in (2) above was suspended in 50 mM Tris-HC1, pH 7.3, 0.1% SDS so as to give a concentration of 200 μg protein/ml and solubilized by boiling for 5 min. After allowing to cool, endoproteinase Lys-C was added to the solution such that the ratio of the protein as the surface active agent insoluble fraction and the Lys-C was 50:1 (wt/wt), and incubated at 37° C. for 3 hours.

Of the K-protein solution digested by Lys-C, a portion corresponding to 500 pmoles of K-protein was fractionated by reversed phase chromatography. The column used was Senshu Pac VP-318-1251 4.6ϕ×250 mm. Elution was performed with a $CH_3CN$ gradient (24% $CH_3CN$, 0.1% TFA–66% $CH_3CN$, 0.1% TFA) at a flow rate of 1 ml/min. Among the fractions of eluant, the amino acid sequence was determined for two fractions of high peptide content (fractions eluted by 55.7–57.0% $CH_3CN$ and 59.3–60.5% $CH_3CN$) using a Gas Phase Sequencer 470-A manufactured by Applied Biosystems Co. The amino acid sequence was determined by the method in accordance with the supplier's manual. As a result, it was found that the K-protein has following two sequences, in the molecule, that is, (1)Thr-Leu-Arg-Gln-His-Tyr-Ser-Ser-Leu-Ile-Pro-Asn-Leu-Phe-Ile-Ala-Ala-Val-Gly-Asn-Ile-Asn-Glu-Leu-Asn-Asn-Ala-AsP-Gln-Ala-Ala-Arg-Glu-Leu-Phe-Leu-Asp-Trp-Asp-Thr (SEQ ID No: 1), and (2)Asn-Lys-Thr-Asp-Phe-Ala-Glu-Ile-Glu-Leu-Tyr-AsP-Val-Leu-Tyr-Thr-Asp-Ala-Asp-Ile-Ser-Gly-Asp-Ala-Pro-Leu-Leu-Ala-Pro-Ala-Tyr-Lys (SEQ ID No: 2).

EXAMPLE 2

Isolation of K-protein qene (1) Preparation of gene library

Chromosomal DNA was prepared from *Brevibacterium lactofermentum* 2256 (ATCC 13869) by a method of Saito and Miura (Biochem. Biophys.Acta., 8278 (1963) 619–629). Two units of Sau3AI were added to about 50 μg of chorosomal DNA and partially digested by incubation at 37° C. for 40 min. The reaction mixture was centrifuged on a sucrose density gradient (10%–40%) at 120,000×g for 26 hours to fractionate the DNA fragments.

Fractions from about 1,500 to 6,000 bps were recovered (1.5 ml volume), which were dialyzed at 4° C. in a TE buffer (10 mM Tris-HCl, 1 mM EDTA, pH 8.0). The Seamless Cellulose Tubing Size 8/32 manufactured by Sanko Junyaku Co. was used as a dialyzing tube. Dialysis was applied for 4 hours with 2 liters of buffer and, conducted for an additional 2 hours after exchanging the buffer.

After dialyis, the chromosomal DNA fraction of 1,500–6,000 bps was extracted with 2-butanol in accordance with a method of Maniatis, et al.(Molecular Cloning second edition, Cold Spring Harbor Press (1989) Maniatis, et al), and then the DNA fragments were ligated to vector pSTV28 which was previously cleaved with BamHI (manufactured by Takara Shuzo Co.) by using T4DNA ligase (manufactured by Takara Shuzo Co.). *Escherichia coli* JM109 (manufactured by Takara Shuzo Co.) was transformed by the resultant ligation mixture in accordance with the supplier's manual of Takara Shuzo Co. to prepare a gene library consisting of about 5,000 clones. It is considered that a host harboring a vector in which the K-protein gene fragment is cloned becomes fetal if the K-protein gene is expressed at a high rate, therefore, a low copy number vector pSTV28 was used.

(2) Cloning of K-protein gene

Based on the amino acid sequence in Example 1 (3-2), a 30 mer oligonucleotide having a sequence of 5'-TTCATCGCTGCTGTCGGCAACATCAACGAG-3' (SEQ ID No:3) was synthesized by using a DNA synthesizer manufactured by Applied Biosystems Co., as a probe used for colony hybridization. Upon determination of the amino acid sequence, presence of degeneration codons corresponding to some amino acid residues results in a significant hindrance and it is essential to cope with this. In the present invention, it is possible to prepare an excellent probe by considering the two points described belows, which is a large factor in the success. The two points are: (1) it was possible to select an amino acid region in which the degree of degeneracy of the codons corresponding to each amino acid is low since an amino acid sequence of a relatively long region can be determined and (2) although there was no definite knowledge regarding the frequency of codon usage of Brevibacterium, the knowledge of Tsuchiya, et al. from cloning lipase (Japanese Patent Laid-Open Publication 92-271780) was referred to.

A colony hybridizing with the probe was obtained from the prepared gene library by colony hybridization. A HYBOND-N™ (nylon membrane) (manufactured by Amersham Co.) membrane was used to make a replica of the colony, hybridization was performed at 50° C. for 40 hours and then the filter was washed four times under the conditions at 40° C. for one hour. Secondary screening was performed on the hyridization-positive colonies by colony hybridization. Using the oligonucleotide described above as a probe and Hybond-N (manufactured by Amersham Co.) as the membrane for preparing a replica, hybridization was performed at 50° C. for 24 hours, and washing was performed three times at 40° C. for one hour and twice at 50° C. for one hour. Twelve clones were selected in the secondary screening. Plasmid DNAs were recovered by the alkali-SDS method from these 12 colonies which were positive in this secondary screening. Results of the cleavage patterns of these plasmids after digestion with Eco RI and HindIII (both manufactured by Takara Shuzo Co.) confirmed that each of the plasmids had an inserted DNA fragment at the BamHI site of pSTV28.

The obtained DNA fragments were blotted on to HYBOND-N™ (nylon membrane) membrane using Vacu-Gene (manufactured by Pharmacia LKB Biotechnology Co.) in accordance with the supplier's manual and Southern hybridization was performed using the oligonucleotide probe described above. Hybridization was performed at 50° C. for 26 hours and washing was performed once at 40° C. for one hour and once at 50° C. for one hour. As a result, it was found that 6 out of the 12 clones which were positive in the secondary screening are hybridized with the probe and the 6 clones could be classified into three types based on a restriction enzyme cleavage pattern.

The nucleotide sequences of these three types of inserted DNA fragments were determined by a dideoxy method using the oligonucleotide described above as the primer, and it was found that one type of DNA fragment contained a sequence of 5'-AACAATGCAGATCAGGCTGCACGT-GAGCTCTTCCTCGATTGGGACACC-3' (SEQ ID NO:4). This sequence codes for the amino acid sequence located on the carboxy terminal side of a potion used to determinate the sequence of the probe from the amino acid sequence determined previously, that is, Asn-Asn-Ala-Asp-Gln-Ala-Ala-Arg-Glu-Leu-Phe-Leu-Asp-Trp-Asp-Thr (corresponding to amino acid Nos. 25–40 in SEQ ID No:1,) and, from this, it was confirmed that the DNA fragment contains at least a portion of the desired gene.

Then, the nucleotide sequence was determined for the entire length of the inserted DNA fragment by the dideoxy method. The determined base sequence is shown in the sequence table, SEQ ID No:5. It was found that the fragment coded for the K-protein. The amino acid sequence of the K-protein deduced from the nucleotide sequence is also described in the sequence table, SEQ ID No:5.

EXAMPLE 3

Preparation of K-protein-deficient strain (1) Preparation of K-protein-deficient strains Using *Brevibacterium lactofermentum* 2256 strain(ATCC 13869) as a parent strain, mutagenesis with N-methyl-N'-nitro-N-nitrosoguanidine (NTG) was applied to whole cells. Cells of 2256 strain were cultivated in 2×TY medium (1.6% Bacto-trypton, 1% Yeast extract, 0.5% NaCl) and the cells were collected when optical absorption of the medium at 660 nm reached about 0.3. After washing the cells with a TM buffer solution of the composition shown in Table 1, they were suspended in an NTG solution (NTG dissolved in TM buffer solution at 0.2 mg/ml), and incubated at 37° C. for 0–90 min. The NTG-treated cells were washed with the TM buffer solution and 2×TY medium and then cultivated in the 2×TY medium overnight to complete mutagenesis.

TABLE 1

| Ingredient | Concentration |
| --- | --- |
| Tris | 50 mM |
| Maleic acid | 50 mM |
| $(NH_4)_2SO_4$ | 1 g/L |
| $MgSO_4.7H_2O$ | 0.1 g/L |
| $Ca(NO_3)_2$ | 5 mg/L |
| $FeSO_4.7H_2O$ | 0.25 mg/L |
| Adjusted to pH 6.0 with NaOH | |

Single colony isolation was performed for cells mutagenized with NTG as described above and about 1,000 colonies were isolated. Each of the clones forming these colonies was examined to determine K-protein was depleted. A cell surface layer fraction was prepared for each of the clones by the method described in Example 1 (1) and a SDS-polyacrylamide gel electrophoresis experiment was performed using the prepared fraction as the specimen. In this way, a strain in which fraction a band of K-protein was not detected around the molecular weight of 63,000, namely, the K-protein-deficient strain was obtained. This strain was named *Brevibacterium lactofermentum* YSR.

The chromosomal DNA of the YSR strain was examined for whether the cause of the deficiency in the K-protein was derived from the gene. That is, the K-protein gene was cloned from the YSR strain to analyze the structure in the same manner as in Example 1.

A chromosomal DNA was prepared from the YSR strain by the method of Saito-Miura (Blochem. Biophys. Acta., 8278 (1963) 619–629). About 50 μg of the DNA was added to two units of Sau3AI and partially digested by incubation at 37° C. for 40 min. Then the digested DNA was fractionated by centrifugation (120,000×g, 26 hours) on a sucrose density gradient (10% to 40%).

Fractions corresponding to about 1,500–6,000 bps were collected (1.5 ml volume), and dialyzed against TE buffer (10 mM Tris/HCl, 1 mM EDTA, pH 8.0) at 4° C. Seamless Cellulose Tubing Size 8/32 manufactured by Sanko Junyaku Co. was used as a dialyzing tube. Dialysis was applied with 2 liters of buffer for 4 hours and then applied for an additional 2 hours after replacing the buffer.

The chromosomal DNA of 1,500–6,000 bps was extracted with 2-butanol according to the method of Maniatis, et al. (Molecular Cloning second edition, Cold Spring Harbor Press (1989) Maniatis, et al) and was ligated to vector pUC18 previously cleaved with BamHI (manufactured by Takara Shuzo Co.) using T4DNA ligase (manufactured by Takara Shuzo Co.). Then *Escherichia coli* JM109 (manufactured by Takara Shuzo Co.) was transformed with the ligation mixture according to the supplier's manual to prepare a gene library.

From the resulting gene library, clones possessing the K-protein gene were screened by colony hybridization using a synthetic DNA having a sequence of 5'-TTCATCGCT-GCTGTCGGCAACATCAACGAG-3' (SEQ ID NO: 3) obtained in Example 2 (2) as the probe. HYBOND-N™ (nylon membrane) (manufactured by Amersham Co.) membrane was used to make a replica of the colonies, hybridization was conducted at 50° C. for 40 hours and washing was performed four times at 40° C. for one hour. Secondary screening was performed on hybridization-positive colonies by colony hybridization. Using the DNA described above as the probe and HYBOND-N™ (nylon membrane) (manufactured by Amersham Co.) as the membrane for preparing replicas, hybridization was performed at 50° C. for 24 hours and washing was three times at 40° C. for one hour and twice at 50° C. for one hour.

Plasmid DNAs were recovered by the alkali-SDS method from these colonies which were positive in this secondary screening. The inserted DNA fragment of the clone expected to contain the whole K-protein gene by restriction enzyme cleavage patterns was sequenced by the dideoxy method. From the result, it is shown that the K-protein gene isolated from the YSR strain has a sequence as shown in the sequence table, and by SEQ ID No:7. When the sequence was compared with SEQ ID No:5, it was found that the K-protein gene of YSR has the mutations shown below. The nucleotide numbers in Table 2 correspond to the base numbers in SEQ ID No:7.

TABLE 2

| nucleotide No. | Type of Mutation |
| --- | --- |
| 932 | G insertion |
| 945 | T → C mutation |
| 948 | A insertion |
| 1031 | A insertion |
| 1215–1216 | CG insertion |
| 1238 | T insertion |
| 1551–1579 | 29 base insertion |
| 1688 | C insertion |
| between 1789 and 1790 | C deletion |
| 2203–2204 | AG insertion |
| 2274 | C insertion |
| 2422 | C insertion |
| 2438 | T insertion |

It was found that the K-protein gene on the chromosome of the YSR strain caused frame shifts by deletion and insertions of the nucleotides as described above and, as a result, the YSR strain no longer expressed the K-protein. The plasmid containing the mutant K-protein gene fragment is named pMAK701. *Escherichia coli* bacteria AJ 12759 possessing the plasmid pMAK701 was deposited to National Institute of Bioscience and Human Technology, Agency of Industrial Science and Technology (1-3, Higashi 1-chome, Tsukuba-shi, Ibaraki-ken, Japan; zip code 305) on January 11, 1993 under the deposition number of FERM P-13364, transferred from the original deposition to international deposition based on Budapest Treaty on Jan. 11, 1994 and has been deposited as Deposition No. FERM BP-4533.

By the way, the plasmid containing the DNA fragment having the base sequence described in the sequence table, and as SEQ ID No:5 is not deposited. However, it will be obvious to those skilled in the art to introduce site-directed mutagenesis to the gene by a method, for example, a PCR method or a method of utilizing a U-containing single stranded DNA. Accordingly, a plasmid containing a DNA fragment having the base sequence described in the sequence table, SEQ ID No: 5 can be prepared easily using pMAK701 as the starting material.

(2) Preparation of a K-protein gene disrupted strain

Figure 1:
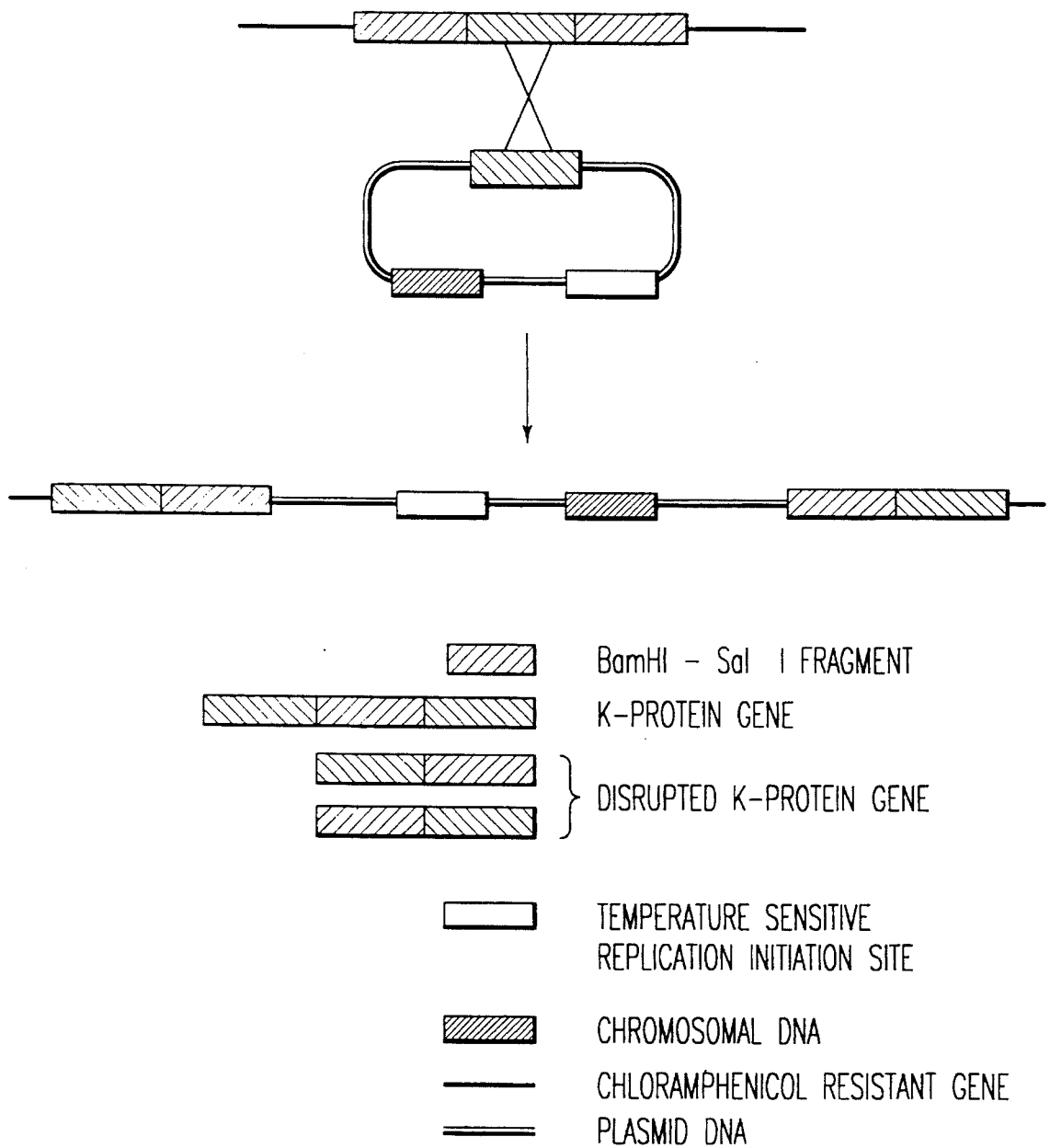
FIG. 1: schematic view for the gene disruption by homologous recombination.

From the DNA fragment containing the K-protein mutant gene obtained in Example 3 (1), a BamHI-SalI fragment having about 650 base pairs in length was excised and ligated to the BamHI-SalI site of the vector pHSC4 having a temperature sensitive replication initiation point (Sugimoto, et al., French Patent Laid-Open Publication No. 2667875/1992) to prepare a plasmid for gene disruption, pMAK705. pMAK705 was introduced into *Brevibacterium lactofermentum* 2256 (ATCC 13869) with AEC (S-(2-aminoethyl)-L-cystein) resistance (referred to herein as AEC$^r$ 2256 strain) by way of an electric pulse method (Sugimoto et al., Japanese Patent Laid-Open Publication 90-207791). The transformants were cultivated at a plasmid replication inhibiting temperature so that the chromosomal K-protein gene was disrupted by homologous recombination in the Bam HI-Sal I region of the K-protein gene. A view of the mechanism of gene disruption is shown in FIG. 1. The BamHI-SalI fragment of the mutant K-protein gene corresponds to the region from the BamHI site (nucleotide number 1156–1161 in SEQ ID No:7) to the SalI site (1704–1709) of the sequence shown in SEQ ID No:7, which is present in the ORF (Open Reading Frame) shown in SEQ ID No:5. Accordingly, one of two copies of the disrupted K-protein genes resulting from the homologous recombination depletes most of 3' side of ORF while the other depletes most of 5' side of ORF. Details of the experiment will be described.

AEC$^r$ 2256 strain possessing pMAK705 was cultivated in a CM2G medium containing 5 μg/ml of chloramphenicol overnight. The culture broth was diluted with a CM2G medium to $10^{-3}$ and 100 μl thereof was spread on a CM2G plate containing 5 μg/ml of chloramphenicol. Cultivation was performed at 34° C. (replication inhibitive temperature) overnight to select chloramphenicol resistant bacteria. Cell surface layer fractions for two chloramphenicol resistant strains thus obtained were prepared by the method as described in Example 1 and were subjected to SDS-polyacrylamide gel electrophoresis to confirm deficiency of the K-protein. The two strains of K-protein-deficient strain were named AJ 12760 and AJ 12956, respectively. The growth rate of the AJ 12760 and AJ 12956 were equal to that of the AEC$^r$ 2256 strain.

The K-protein-deficient strain AJ 12760 was deposited to National Institute of Bioscience and Human Technology, Agency of Industrial Science and Technology (1-3, Higashi 1-chome, Tsukuba-shi, Ibaraki-ken, Japan; zip code 305)on Jan. 11, 1993 as FERM P-13365 and transferred on Jan. 11, 1994 from the original deposition to international deposition based on the Budapest Treaty and deposited with a deposition No. FERM BP-4534. Further, K-protein-deficient strain AJ 12956 was internationally deposited based on the Budapest Treaty on Jan. 11, 1994 to National Institute of Bioscience and Human Technology, Agency of Industrial Science and Technology (1-3, Higashi 1-chome, Tsukuba-shi, Ibaraki-ken, Japan; zip code 305) with the deposition No. as FERM BP-4532.

(3) Ammonium incorporation activity of K-protein-deficient strain

Figure 2:
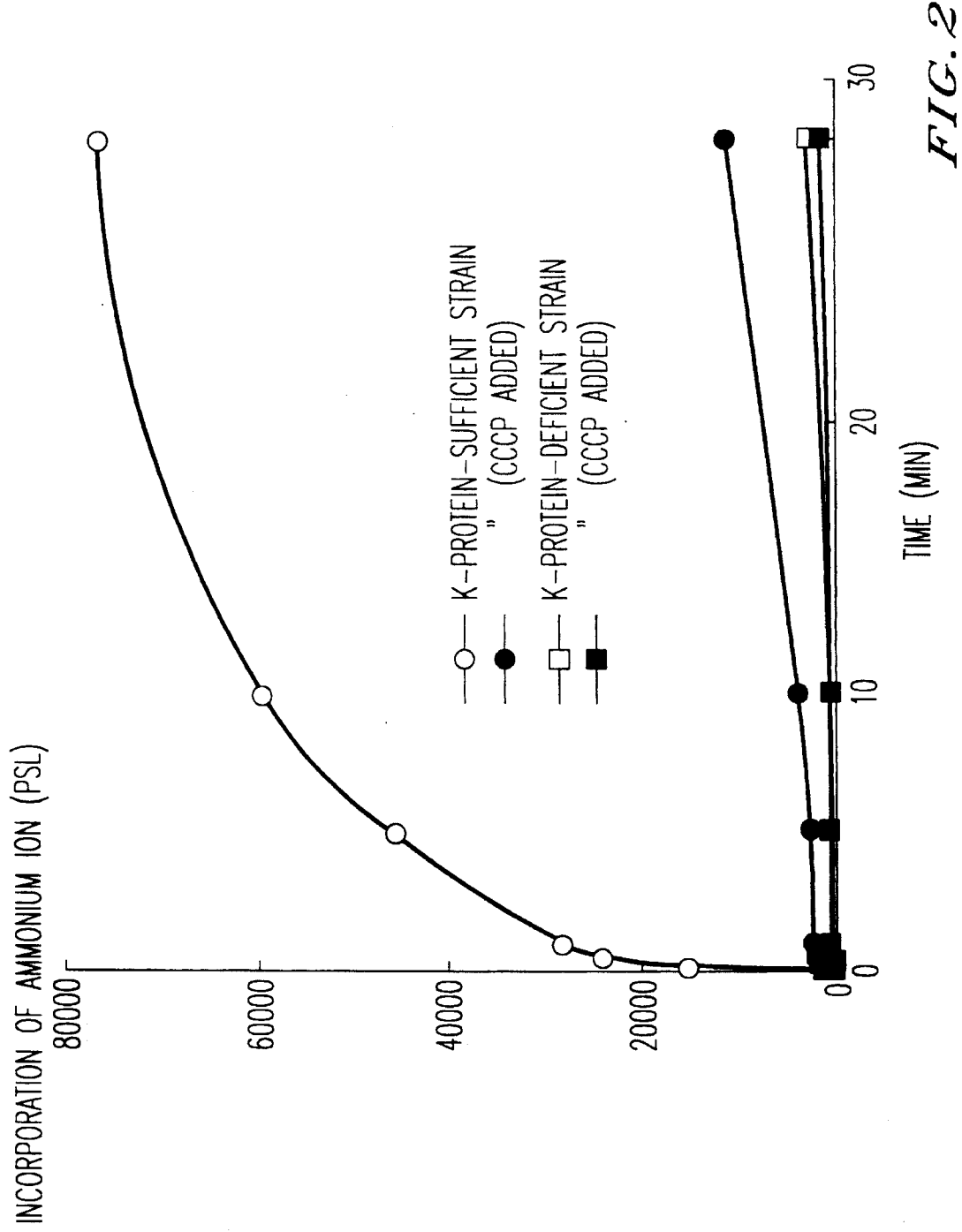
FIG. 2: shows contribution of K-protein to incorporation of ammonium ions. ○ ... K-protein-sufficient strain (AEC$^r$ 2256) ● ... K-protein-sufficient strain (AEC$^r$ 2256), CCCP carbonylcyanide m-chlorophenyl hydrazine) added □ ... K-protein-deficient strain (AJ 12760) ■ ... K-protein-deficient strain (AJ 12760), CCCP added

When ammonium incorporation activity of the K-protein-deficient strain AJ 12760 prepared in (1) above was measured, a remarkable reduction was observed as compared with the AEC$^r$ 2256 strain as shown in FIG. 2. Measurement of ammonium incorporation was performed using $^{14}C$ labeled methyl ammonium, an analogue of ammonium ions, as a substrate and according to a rapid filtration method (A. Jayakumar, et al., Analytical Biochemistry, 135 (1983) 475–478). From the result, it is shown that the K-protein is a novel cell surface layer protein contributing to the incorporation of nutrients in Coryneform bacteria.

Details for the experiment measuring ammonium incorporation activity of the K-protein-deficient strain AJ 12760 are shown below. Bacterial cells for which the incorporation activity was measured were inoculated from a CM2G agar plate to a CM2G liquid medium and cultivated at 30° for overnight. After cooling the culture broth in iced water, cells were collected and washed twice with a previously ice cooled buffer B (50 mM Tris-HCl, pH 6.8, 100 mM NaCl) and suspended in a buffer B to give a density of $2.0 \times 10^8$ cells/ml. 100 μl of cell suspension was placed in a well of Multi-Screen HA manufactured by Milipore Co. to which glucose was added to a final concentration of 10 mM as an energy source and kept at 30° C. for 5 min. In this course, CCCP (carbonylcyanide m-chlorophenylhydrazone (manufactured by Sigma Co.)) was presented as a decoupling agent if necessary (final concentration at 20 μM).

The ammonia incorporating reaction was started by adding $^{14}C$-labelled methyl ammonium to each of wells to a final concentration of 20 μM. After maintaining 25° C. for a predetermined period of time, the reaction solution was rapidly removed from each of the wells by aspiration to terminate the reaction. After aspiration, cells held on the Multi-Screen HA membrane was washed with a buffer C (50 mM Tris-HCl, pH 6.8, 1M NaCl) and, after drying the membrane, $^{14}C$ radioactivity incorporated into the cells was measured by using a Bio-imaging Analyzer (BAS-2000, manufactured by Fuji Photographic Film Inc.)

EXAMPLE 4

Precipitation property of K-protein-deficient strain

Precipitation property of the K-protein-deficient strain in the culture medium was evaluated. AJ 12760, AJ 12956 and YSR were used as the K-protein-deficient strains. In addition, *Brevibacterium lactofermentum* 2256 (ATCC 13869) and $AEC^r$ 2256 as the K-protein-sufficent strains were used as a control. Each strain of AJ 12760, AJ 12956, YSR, 2256 and $ACE^r$ 2256 was cultivated overnight on a CM2G plate containing 20 μg/ml of chloramphenicol and one platinum loop of each cells (amount corresponding to 1/40 of a plate) was inoculated to a main liquid culture medium and cultivated at 31.5° C. for 24 hours. For the main liquid culture medium, 20 ml of a liquid culture medium of the following composition was placed in a 500 ml volume Sakaguchi flask, adjusted to pH 8.0 by using KOH, heat sterilized at 115° C. for 10 min and then $CaCO_3$ sterilized under dry heating at 200° C. for three hours was added additionally.

TABLE 3

| Composition for Culture Medium) | |
|---|---|
| Ingredient | Amount of blend |
| Glucose or sucrose | 10 g/100 mL |
| $(NH_4)_2SO_4$ | 5.5 g/100 mL |
| $KH_2PO_4$ | 0.1 g/100 mL |
| $MgSO_4.7H_2O$ | 0.1 g/100 mL |
| $FeSO_4.7H_2O$ | 0.001 g/100 mL |
| $MnSO_4.4H_2O$ | 0.001 g/100 mL |
| "Mame no" (hydrolyzate of soybean protein)* | 0.05 g/100 ml (as tatal nitrogen) |
| Vitamin B1 hydrochloride | 200 g/L |
| Biotin | 500 g/L |
| GD-113 (defoamer: manufactured by Nippon Yushi Co.) | 0.002 mL/100 mL |
| $CaCO_3$ (sterilized by dry heating at 200 C. for 3 hrs) | 5.0 g/100 mL |

*The "mame no" contains 3.49 g nitrogen/100 ml

Cultivation of each of the K-protein deficient and K-protein-sufficient strains was performed by a duplicate system using a medium containing glucose and a medium containing sucrose. Table 4 shows the carbon source and pH measured after cultivation for each of cultivated specimens.

TABLE 4

| Specimen No. | Strain | Carbon Source | pH |
|---|---|---|---|
| 1 | 2256 | glucose | 6.48 |
| 2 | 2256 | sucrose | 6.30 |
| 3 | YSR | glucose | 6.28 |
| 4 | YSR | sucrose | 6.18 |
| 5 | $AEC^r2256$ | glucose | 6.20 |
| 6 | $AEC^r2256$ | sucrose | 6.32 |
| 7 | AJ 12760 | glucose | 5.93 |
| 8 | AJ 12760 | sucrose | 5.74 |
| 9 | AJ 12956 | glucose | 5.88 |
| 10 | AJ 12956 | sucrose | 5.78 |
| 11 | 2256 | glucose | 6.28 |
| 12 | 2256 | sucrose | 6.20 |
| 13 | YSR | glucose | 6.24 |

TABLE 4-continued

| Specimen No. | Strain | Carbon Source | pH |
|---|---|---|---|
| 14 | YSR | sucrose | 6.14 |
| 15 | $AEC^r2256$ | glucose | 6.26 |
| 16 | $AEC^r2256$ | sucrose | 6.38 |
| 17 | AJ 12760 | glucose | 5.99 |
| 18 | AJ 12760 | sucrose | 5.79 |
| 19 | AJ 12956 | glucose | 5.90 |
| 20 | AJ 12956 | sucrose | 5.77 |

Among duplicates cultivated in glucose and sucrose, a precipitation test was applied to one set (specimen Nos. 1–10) while leaving the culture medium as it was after cultivation for the other set (specimen Nos. 11–20) and adjusting pH to 4.0 of the culture medium after cultivation. pH 4.0 is a condition usually used in purifying L-lysine-HCl by ion exchange chromatography.

A precipitation test was conducted as described below. Each 15 mL culture medium after cultivation was transferred to a test tube of 15 mm inner diameter and allowed to spontaneously precipitate cells. After a predetermined period of time, a position at the boundary between supernatants resulting from precipitation of the cells and the precipitated portion in which the cells were suspended was measured to calculate the relative precipitation degree by the formula described below, while assuming the ratio (%) of the distance b which is from the surface of medium to the boundary to the height a of the surface of medium as "supernatant ratio". The cell concentration was measured based on optical absorption at 562 nm ($OD_{562}$) when the culture medium was diluted 26 fold. Further, the height a of the surface of medium when 15 mL of the medium was transferred to a test tube was 9 cm. The dry cell weight was calculated by conversion from $OD_{562}$ in accordance with a previously prepared conversion equation.

$$\text{(Relative precipitation degree)} = \frac{\text{(Cell density in precipitation portion)}}{\text{(Total cell concentration)}} \times 100$$

(Cell density in precipitation portion) =

$$\frac{\text{(dry cell weight in homogeneous state)} \times 100 - \text{(dry cell weight in supernatant)} \times \text{(supernatant ratio)}}{100 - \text{(supernatant ratio)}}$$

(Supernatant ratio)=$(b/a) \times 100$ a; height of the surface of medium (that is, total height of the supernatant portion and the precipitation protion)

b; distance from the surface of medium to the boundary (that is, a numerical value obtained by subtracting the boundary height from a)

Figure 3:
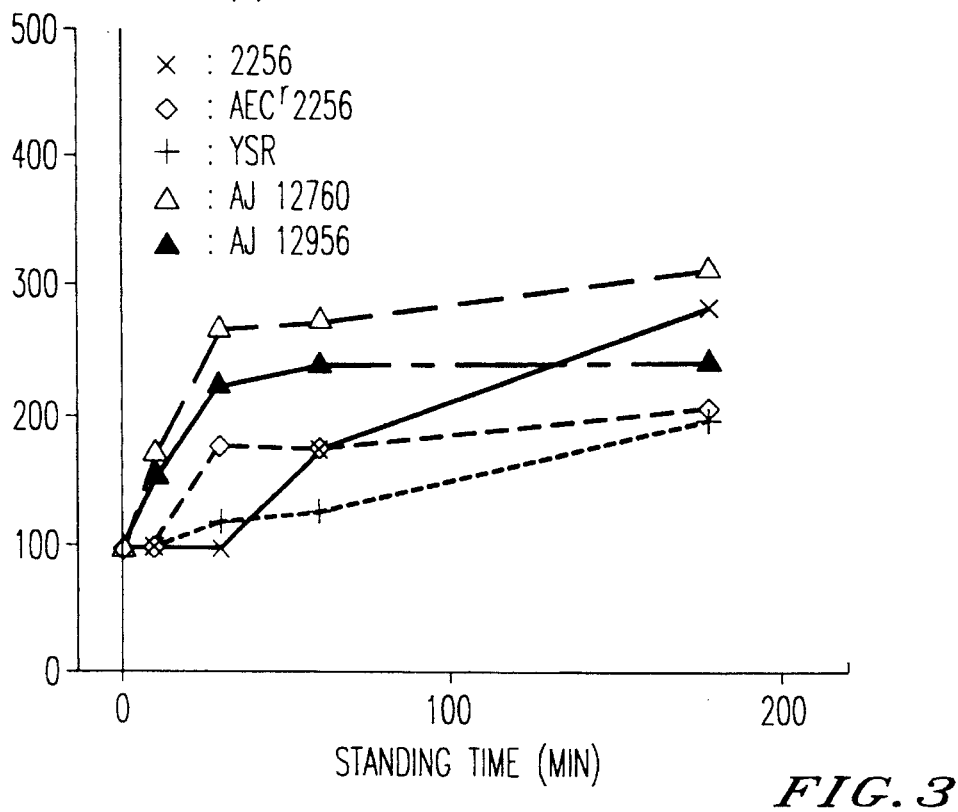
FIG. 3: diagram showing precipitation of K-protein-deficient and K-protein-sufficient strains (Carbon source: glucose, culture medium after completion of cultivation adjusted to pH 4.0). × ... 2256 strain (ATCC 13869) + ... YSR strain ◊ ... AEC$^r$ 2256 strain △ ... AJ 12760 ▲ ... AJ 12956

(Dry cell weight)=$1.586(OD_{562})^3 - 1.446(OD_{562})^2 - 1.396(OD_{562}) - 0.013$ The total cell density (total cell OD), the distance from the surface of medium to the boundary (b), the height of the surface of medium (a) and the cell density in the supernatant (supernatant OD) in each of the cultivation lots were measured immediately after, 10 min after, 30 min after, 60 min after, 180 min after and 23 hr after transferring the culture medium to the test tube and the results are shown in Tables 5 and 6. The value of relative precipitation degree of each time is calculated and the results are shown in Tables 7 and 8. Further, change of the relative precipitation degree over time was illustrated for specimens 1, 3, 5, 7 and 9 in FIG. 3, for specimens 2, 4, 6, 8 and 10 in FIG. 4, for specimens 11, 13, 15, 17 and 19 in FIG. 5 and for specimens 12, 14, 16, 18 and 20 in FIG. 6.

From the foregoing results, it has been found that cells were precipitated in a shorter period of time (10–30 min) irrespective of the kind of the carbon source used in the culture medium and adjustment or non-adjustment of the pH value in the culture medium after completion of cultivation for the K-protein gene disrupted strains AJ 12760 and AJ 12956. Further, it has been found that cells of the K-protein deficent mutant YSR were precipitated in a short period of time in the same manner as the K-protein gene disrupted strains when they are cultivated using sucrose as the carbon source and stood still after completion of cultivation without adjusting pH. On the contrary, cells of the AEC$^r$ 2256 and 2256 as the K-protein-sufficient strains were not substantially precipitated even if the culture medium was stood still 30 min after completion of cultivation. Particularly, precipitation of the cells was not recognized even after 23 hours if they were stood still without adjusting the pH of the culture medium.

For the precipitation degree of the cells, measurements of the precipitation constant of cell aggregation products give the same result as the relative precipitation degree measured as described above.

INDUSTRIAL APPLICABILITY

The present invention provides a novel cell surface layer protein that contributes to the incorporation of nutrients in Coryneform bacteria and the gene thereof, as well as providing the transformant obtained by introduction and amplifying the gene in the cells of Coryneform bacteria. Further, it also improves a process for producing L-amino acid by a fermentation method using Coryneform bacteria having an activity to produce L-amino acid as a host for the transformant and improving the process for producing the L-amino acid by the fermentation method using the host bacteria.

TABLE 5

| specimen No. | total cell OD | 0 | | 10 min | | 30 min | | 60 mim | | 180 mim | | 23 hr | |
|---|---|---|---|---|---|---|---|---|---|---|---|---|---|
| | | b (mm) | sup OD | b (mm) | sup OD | b (mm) | sup OD | b (mm) | sup OD | b (mm) | sup OD | b (mm) | sup OD |
| 1 | 1.30 | 0 | 1.30 | 0 | 1.20 | 0 | 1.15 | 0 | 1.18 | 0 | 1.08 | 0 | 1.03 |
| 2 | 1.30 | 0 | 1.30 | 0 | 1.20 | 0 | 1.11 | 0 | 1.11 | 0 | 0.96 | 0 | 0.91 |
| 3 | 1.21 | 0 | 1.21 | 0 | 1.00 | 70 | 1.05 | 65 | 1.08 | 30 | 0.56 | 65 | 0.47 |
| 4 | 1.20 | 0 | 1.20 | 0 | 1.08 | 70 | 1.02 | 70 | 1.01 | 66 | 0.74 | 63 | 0.65 |
| 5 | 0.51 | 0 | 0.51 | 0 | 0.50 | 0 | 0.49 | 0 | 0.50 | 0 | 0.42 | 5 | 0.15 |
| 6 | 0.46 | 0 | 0.46 | 0 | 0.44 | 0 | 0.42 | 0 | 0.42 | 0 | 0.35 | 4 | 0.22 |
| 7 | 1.05 | 0 | 1.05 | 45 | 0.62 | 50 | 0.52 | 55 | 0.48 | 60 | 0.28 | 55 | 0.17 |
| 8 | 1.05 | 0 | 1.05 | 55 | 0.70 | 52 | 0.54 | 50 | 0.47 | 55 | 0.25 | 60 | 0.32 |
| 9 | 1.10 | 0 | 1.10 | 50 | 0.90 | 45 | 0.65 | 45 | 0.55 | 50 | 0.38 | 50 | 0.31 |
| 10 | 1.07 | 0 | 1.07 | 50 | 0.72 | 50 | 0.53 | 30 | 0.47 | 65 | 0.29 | 55 | 0.33 |

TABLE 6

| specimen No. | total cell OD | 0 | | 10 min | | 30 min | | 60 mim | | 180 mim | | 23 hr | |
|---|---|---|---|---|---|---|---|---|---|---|---|---|---|
| | | b (mm) | sup OD | b (mm) | sup OD | b (mm) | sup OD | b (mm) | sup OD | b (mm) | sup OD | b (mm) | sup OD |
| 11 | 1.25 | 0 | 1.25 | 0 | 1.20 | 0 | 0.00 | 80 | 1.18 | 80 | 1.05 | 80 | 1.15 |
| 12 | 1.25 | 0 | 1.25 | 0 | 1.25 | 0 | 0.00 | 80 | 1.20 | 75 | 1.08 | 75 | 1.10 |
| 13 | 1.10 | 0 | 1.10 | 0 | 1.15 | 60 | 1.05 | 65 | 1.04 | 70 | 0.91 | 70 | 0.85 |
| 14 | 1.05 | 0 | 1.05 | 0 | 1.05 | 0 | 0.00 | 70 | 1.01 | 40 | 0.89 | 70 | 0.92 |
| 15 | 0.44 | 0 | 0.44 | 0 | 0.42 | 70 | 0.37 | 65 | 0.34 | 67 | 0.32 | 70 | 0.28 |
| 16 | 0.44 | 0 | 0.44 | 0 | 0.44 | 60 | 0.41 | 60 | 0.39 | 60 | 0.38 | 65 | 0.29 |
| 17 | 1.25 | 0 | 1.25 | 40 | 0.08 | 60 | 0.05 | 60 | 0.04 | 65 | 0.05 | 75 | 0.03 |
| 18 | 1.15 | 0 | 1.15 | 40 | 0.05 | 50 | 0.05 | 55 | 0.04 | 57 | 0.05 | 60 | 0.03 |
| 19 | 1.00 | 0 | 1.00 | 30 | 0.05 | 48 | 0.05 | 50 | 0.04 | 50 | 0.05 | 60 | 0.04 |
| 20 | 1.00 | 0 | 1.00 | 40 | 0.05 | 60 | 0.05 | 65 | 0.03 | 70 | 0.05 | 75 | 0.03 |

TABLE 7

| specimen No. | Relative precipitation degree | | | | | |
|---|---|---|---|---|---|---|
| | 0 | 10 mim | 30 mim | 60 mim | 180 mim | 23 hr |
| 1 | 100 | 100 | 100 | 100 | 100 | 100 |
| 2 | 100 | 100 | 100 | 100 | 100 | 100 |
| 3 | 100 | 100 | 100 | 203 | 145 | 444 |
| 4 | 100 | 100 | 247 | 254 | 317 | 298 |
| 5 | 100 | 100 | 100 | 100 | 100 | 104 |
| 6 | 100 | 100 | 100 | 100 | 100 | 102 |
| 7 | 100 | 168 | 197 | 229 | 298 | 263 |
| 8 | 100 | 216 | 223 | 219 | 285 | 340 |
| 9 | 100 | 158 | 180 | 189 | 232 | 238 |
| 10 | 100 | 188 | 214 | 221 | 458 | 277 |

TABLE 8

| specimen No. | Relative precipitation degree | | | | | |
|---|---|---|---|---|---|---|
| | 0 | 10 mim | 30 mim | 60 mim | 180 mim | 23 hr |
| 11 | 100 | 100 | 100 | 171 | 282 | 633 |
| 12 | 100 | 100 | 100 | 178 | 249 | 600 |
| 13 | 100 | 100 | 117 | 126 | 193 | 380 |
| 14 | 100 | 100 | 100 | 138 | 126 | 567 |
| 15 | 100 | 100 | 177 | 175 | 203 | 600 |
| 16 | 100 | 100 | 120 | 133 | 140 | 533 |
| 17 | 100 | 170 | 268 | 269 | 312 | 475 |
| 18 | 100 | 187 | 239 | 280 | 298 | 340 |
| 19 | 100 | 153 | 225 | 239 | 238 | 340 |
| 20 | 100 | 170 | 265 | 313 | 370 | 475 |

Furthermore, the present invention provides novel Coryneform bacteria being deficient in the cell surface layer protein and having a aggregating property, thereby enabling energy savings in the production of L-amino acid their use.

We claim:

1. Coryneform bacteria having a cell aggregating property and being deficient in a cell surface layer protein having the following two sequences within the molecule:
   (1) Thr-Leu-Arg-Gln-His-Tyr-Ser-Ser-Leu-Ile-Pro-Asn-Leu-Phe-Ile-Ala-Ala-Val-Gly-Asn-Ile-Asn-Glu-Leu-Asn-Asn-Ala-Asp-Gln-Ala-Ala-Arg-Glu-Leu-Phe-Leu-Asp-Trp-Asp-Thr (SEQ ID NO: 1); and
   (2) Asn-Lys-Thr-Asp-Phe-Ala-Glu-Ile-Glu-Leu-Tyr-Asp-Val-Leu-Tyr-Thr-Asp-Ala-Asp-Ile-Ser-Gly-Asp-Ala-Pro-Leu-Leu-Ala-Pro-Ala-Tyr-Lys (SEQ ID NO: 2),
   wherein said protein has a molecular weight of about 63,000 dalton.

2. The Coryneform bacteria of claim 1, wherein a gene coding for the cell surface layer protein, and located on a chromosome, is disrupted by homologous recombination between a DNA fragment containing at least a portion of said gene, and said gene on said chromosome.

3. The Coryneform bacteria of claim 2, wherein said DNA fragment is at least a portion of SEQ ID NO: 5.

4. The Coryneform bacteria of claim 1, wherein the Coryneform bacteria is *Brevibacterium lactofermentum*.

5. The Coryneform bacteria of claim 2, wherein the Coryneform bacteria is *Brevibacterium lactofermentum*.

6. A method of using the bacteria of claims 1, 2, 3 or 4, comprising the steps of:
   cultivating said bacteria having an activity to produce at least one member selected from the group consisting of foreign proteins, amino acids and nucleic acids;
   allowing aggregation and sedimentation of said bacteria.

7. The method of claim 6, wherein said at least one member is an L-amino acid.

8. Coryneform bacteria having a cell aggregating property, wherein said bacteria has a relative precipitation degree selected from the group consisting of:
   at least 180 after 30 minutes when said bacteria is cultivated in a medium containing glucose as a carbon source and pH of the medium is not adjusted after cultivation;
   at least 214 after 30 minutes when said bacteria is cultivated in a medium containing sucrose as a carbon source and pH of the medium is not adjusted after cultivation;
   at least 225 after 30 minutes when said bacteria is cultivated in a medium containing glucose as a carbon source and pH of the medium is adjusted to 4.0 after cultivation; and
   at least 239 after 30 minutes when said bacteria is cultivated in a medium containing sucrose as a carbon source and pH of the medium is adjusted to 4.0 after cultivation.

\* \* \* \* \*